United States Patent
Zhang et al.

(10) Patent No.: US 10,370,323 B2
(45) Date of Patent: Aug. 6, 2019

(54) METHOD FOR PREPARING CHIRAL GAMMA-SECONDARY AMINO ALCOHOL

(71) Applicants: SHANGHAI JIAO TONG UNIVERSITY, Shanghai (CN); NIPPON CHEMICAL INDUSTRIAL CO., LTD., Tokyo (JP)

(72) Inventors: Wanbin Zhang, Shanghai (CN); Zhenfeng Zhang, Shanghai (CN); Qiupeng Hu, Shanghai (CN)

(73) Assignees: SHANGHAI JIAOTONG UNIVERSITY, Shanghai (CN); NIPPON CHEMICAL INDUSTRIAL CO., LTD., Tokyo (JP)

( * ) Notice: Subject to any disclaimer, the term of this patent is extended or adjusted under 35 U.S.C. 154(b) by 38 days.

(21) Appl. No.: 15/514,243

(22) PCT Filed: Sep. 23, 2015

(86) PCT No.: PCT/CN2015/090359
§ 371 (c)(1),
(2) Date: Mar. 24, 2017

(87) PCT Pub. No.: WO2016/045589
PCT Pub. Date: Mar. 31, 2016

(65) Prior Publication Data
US 2017/0275240 A1    Sep. 28, 2017

(30) Foreign Application Priority Data
Sep. 26, 2014    (CN) .......................... 2014 1 0503201

(51) Int. Cl.
C07C 213/00    (2006.01)
C07D 333/16    (2006.01)
C07D 333/20    (2006.01)
C07D 307/42    (2006.01)
C07D 307/52    (2006.01)
C07D 317/58    (2006.01)
C07B 53/00    (2006.01)

(52) U.S. Cl.
CPC ............ *C07C 213/00* (2013.01); *C07B 53/00* (2013.01); *C07D 307/42* (2013.01); *C07D 307/52* (2013.01); *C07D 317/58* (2013.01); *C07D 333/16* (2013.01); *C07D 333/20* (2013.01); *C07B 2200/07* (2013.01)

(58) Field of Classification Search
CPC .................................................. C07C 213/00
See application file for complete search history.

(56) References Cited

FOREIGN PATENT DOCUMENTS

CN    102000606 A    4/2011
WO    2006/054644 A1    5/2006

OTHER PUBLICATIONS

Liu, D., et al. "Practical Synthesis of Enantiopure γ-Amino Alcohols by Rhodium-Catalyzed Asymmetric Hydrogenation of β-Secondary-Amino Ketones." Angew. Chem. Int. Ed. (2005), vol. 44, pp. 1687-1689.*
Hu, Q., et al. "ZnCl2-Promoted Asymmetric Hydrogenation of β-Secondary-Amino Ketones Catalyzed by a P-Chiral Rh-Bisphosphine Complex." Angew. Chem. Int. Ed. (2015), vol. 54, Published Online: Dec. 29, 2014. Accessed Aug. 21, 2018, pp. 2260-2264. (Year: 2014).*
The Chemical Company. "Methanol." (Jul. 11, 2012). Accessed Aug. 22, 2018. Available from: < https://thechemco.com/chemical/methanol/ >. (Year: 2012).*
"Convert atm to bar—Conversion of Measurement Units." (Mar. 13, 2012). Accessed Aug. 22, 2018. Available from: < https://web.archive.org/web/20120313005449/https://www.convertunits.com/from/atm/to/bar >. (Year: 2012).*
New World Encyclopedia. "Room temperature." (Mar. 9, 2010). Accessed Aug. 22, 2018. (Year: 2010).*
Liu, D., et al. "Practical Synthesis of Enantiopure γ-Amino Alcohols by Rhodium-Catalyzed Asymmetric Hydrogenation of β-Secondary-Amino Ketones." Angew. Chem. Int. Ed. (2005), vol. 44, pp. 1687-1689. (Year: 2005).*

(Continued)

*Primary Examiner* — Andrew D Kosar
*Assistant Examiner* — John S Kenyon
(74) *Attorney, Agent, or Firm* — Westerman, Hattori, Daniels & Adrian, LLP

(57) ABSTRACT

A method for preparing chiral γ-secondary amino alcohol includes: adding into a solvent an acid addition salt of β-secondary amino ketone represented by general formula (1), an alkali, a metal salt additive and a diphosphine-rhodium complex, so as to carry out a reaction in a hydrogen atmosphere and obtain a chiral γ-secondary amino alcohol compound represented by general formula (2). In general formula (2), Ar represents an aryl group with or without substituent group(s), R represents an alkyl group or an aralkyl group, and HY represents an acid. The synthesis scheme has a simple process, the metal salt additive remarkably improves the effect of a rhodium-catalyzed asymmetric hydrogenation technology, and accordingly, the reaction yield and the optical purity of a product are improved, the production process is simplified, production costs are reduced, and the synthesis scheme is highly suitable for mass industrial production.

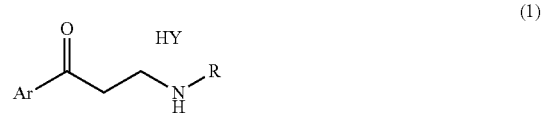

(1)

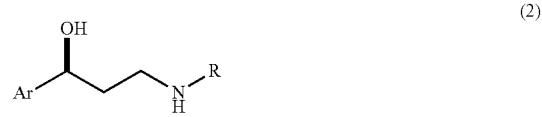

(2)

14 Claims, No Drawings

(56) References Cited

OTHER PUBLICATIONS

Sakuraba et al., Practical Asymmetric Synthesis of (R)-Fluoxetine Hydrochloride Catalyzed by (2S,4S)-4-Dicyclohexylphosphino-2-diphenylphosphinomethyl-1-(N-methylcarbamoyl)pyrrolidine-Rhodium Complex1, Synlett, Sep. 1991, pp. 689, 690 and 982. Cited in Specification. (3 pages).

Sakuraba et al., Efficient Asymmetric Hydrogenation of β- and γ-Amino Ketone Derivatives Leading to Practical Synthesis of Fluoxetine and Eprozinol, Chem. Pharm. Bull., (1995), vol. 43, No. 5, pp. 748-753. Cited in Specification. (6 pages).

Liu et al., Practical Synthesis of Enantiopure γ-Amino Alcohols by Rhodium-Catalyzed Asymmetric Hydrogenation of β-Secondary-Amino Ketones, Feb. 2005, Angew. Chem. Int. Ed., 44, pp. 1687-1689. Cited in Specification. ISR & Written Opinion. (3 pages).

Hu et al., ZnCl2-Promoted Asymmetric Hydrogenation of β-Secondary-Amino Ketones Catalyzed by a P-Chiral Rh-Bisphosphine Complex, Angew. Chem. Int. Ed., (2015), vol. 54, pp. 2260-2264. Cited in ISR. (5 pages).

Written Opinion of the International Searching Authority PCT/ISA/237 and Form PCT/18/373 dated Dec. 16, 2015, of PCT/CN2015/090359 with English Translation (6 pages).

International Search Report dated Dec. 16, 2015, issued in counterpart of International Application No. PCT/CN2015/090359 (14 pages).

\* cited by examiner

METHOD FOR PREPARING CHIRAL GAMMA-SECONDARY AMINO ALCOHOL

TECHNICAL FIELD

The present invention relates to a method for preparing a chiral γ-secondary amino alcohol, more specifically, a synthetic method for preparing a chiral γ-secondary amino alcohol with a catalytic asymmetric hydrogenation technology by using a metal salt additive to improve the activity of a catalytic system of diphosphine-rhodium complex.

BACKGROUND

A backbone of chiral γ-secondary amino alcohol is widely found in various drug molecules and physiologically-active molecules, such as, Duloxetine, Fluoxetine or the like. Duloxetine hydrochloride, chemically named as (S)-N-methyl-3-(1-naphthoxy)-3-(2-thienyl)-1-propylamine hydrochloride, is a reuptake inhibitor against 5-hydroxytryptamine and norepinephrine developed by Eli Lilly and Company (USA), and is clinically applied mainly for treatment of depressive disorder and anxiety. Its global sale of about 5 billions U.S. dollars in the year of 2013 shows a remarkably massive market. Recently, the patent for this drug is to expire, and some drug manufacturers have been approved for its production.

Currently, a chiral γ-secondary amino alcohol is mainly obtained by the means of racemic resolution. However, the traditional resolution technology has a yield of less than 50% and a considerable proportion of isomer is difficult to use, which causes an increase in cost as well as environmental pollution. Synthesis of γ-amino alcohol with asymmetric hydrogenation technology is less studied up to now. In 1991, Professor Achiwa for the first time reported asymmetric synthesis of γ-secondary amino alcohol by catalytic hydrogenation of β-secondary amino ketone using (2S, 4S)-MCCPM as a catalyst, giving an ee value of 90.8% (a) S. Sakuraba, K. Achiwa, Synlett 1991, 689; b) S. Sakuraba, K. Achiwa, Chem. Pharm. Bull. 1995, 43, 748). In 2005, Professor Xumu Zhang reported catalytic asymmetric hydrogenation of β-secondary amino ketone as a substrate using DuanPhos-Rh as a catalyst, giving an ee value as high as 99% and TON of higher than 4500 (D. Liu, W. Gao, C. Wang, X. Zhang, Angew. Chem. Int. Ed. 2005, 44, 1687).

However, in the prior art, inactivation of catalyst caused by the chiral γ-secondary amino alcohol product, which is due to the strong coordination of the nitrogen atom, and instability of the substrate β-secondary amino ketone, makes it difficult to conduct asymmetric hydrogenation of β-secondary amino ketone. Additionally, in the prior art, the chiral γ-secondary amino alcohol has been synthesized by a longer route, and resolution requires a resolving agent, which is expensive and leads to a corrosivity problem to some degree.

SUMMARY

The present invention has been accomplished so as to resolve the above technical problems in the prior art.

In the present invention, a series of metal salt additives are added for the first time to reduce competitive coordination of the nitrogen or oxygen atom in the product for the catalyst of diphosphine-rhodium complex and to improve circulation efficiency of the catalyst. Accordingly, the problem in competitive coordination of such a type of compound in the prior art has been resolved. The goal has been realized to improve circulation efficiency of the catalyst, improve the catalytic reactive activity and enantioselectivity.

That is, the inventive feature of the present invention lies in that the present inventors have found for the first time that metal salt additives can promote the asymmetric hydrogenation of β-secondary amino ketone catalyzed by diphosphine-rhodium complex, and thereby accomplished the present invention.

In the present preparation method, the synthetic efficiency is improved, the enantioselectivity is high, and the synthesis cost is reduced. Accordingly, an industrialized synthesis of the chiral γ-secondary amino alcohol can be realized.

The present invention is accomplished by the following technical solutions.

In the present invention, there is provided a method for preparing a chiral γ-secondary amino alcohol, characterized in the steps of:

adding into a solvent an acid addition salt of β-secondary amino ketone represented by the following general formula (1), an alkali, a metal salt additive and a diphosphine-rhodium complex to perform a reaction in hydrogen atmosphere, so as to obtain a chiral compound of γ-secondary amino alcohol represented by the following general formula (2),

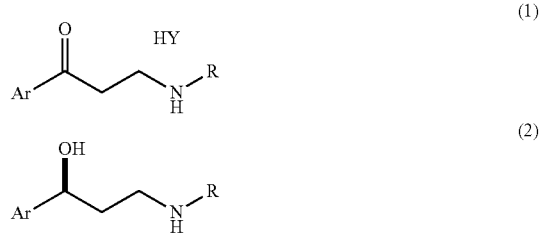

in the general formulas (1) and (2), Ar represents an aryl group with or without substituent group(s), R represents an alkyl group or an aralkyl group, and HY represents an acid.

In the method of the present invention, preferably, in the general formulas (1) and (2), Ar can be any one selected from the group consisting of phenyl, 2-methylphenyl, 3-methylphenyl, 4-methylphenyl, 2-methoxyphenyl, 3-methoxyphenyl, 4-methoxyphenyl, 2-ethoxyphenyl, 3-ethoxyphenyl, 4-ethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 1-naphthyl, 2-naphthyl, 2-trifluoromethylphenyl, 3-trifluoromethylphenyl, 4-trifluoromethylphenyl, 2-furyl, 2-thienyl, 3,4-dimethoxyphenyl, 3,4-dimethylphenyl, 3,4-dichloro phenyl and 3,4-methylenedioxy phenyl. R can be any one selected from the group consisting of methyl, ethyl, propyl iso-propyl, butyl, iso-butyl, tert-butyl, pentyl, iso-pentyl, neo-pentyl, hexyl, heptyl, octyl and benzyl.

In the method of the present invention, preferably, in the general formula (1), HY can be any one selected from the group consisting of hydrochloric acid, sulfuric acid, phosphoric acid, tartaric acid, p-methylbenzenesulfonic acid, trifluoromethanesulfonic acid, salicylic acid, tetrafluoroboric acid, acid and hexafluoroantimonic acid.

In the present method for preparing a chiral γ-secondary amino alcohol, preferably, the diphosphine-rhodium complex is [Rh(L)(L')]X, wherein, L is any one chiral diphosphine ligand selected from the group consisting of (R,R)-*, (R,R)-BenzP*, (R,R)-Miniphos, (S,S)-BisP*, (S,S)-QuinoxP*, (S,S)-BenzP*, (S,S)-Miniphos and (R,R)-BisP* as follows,

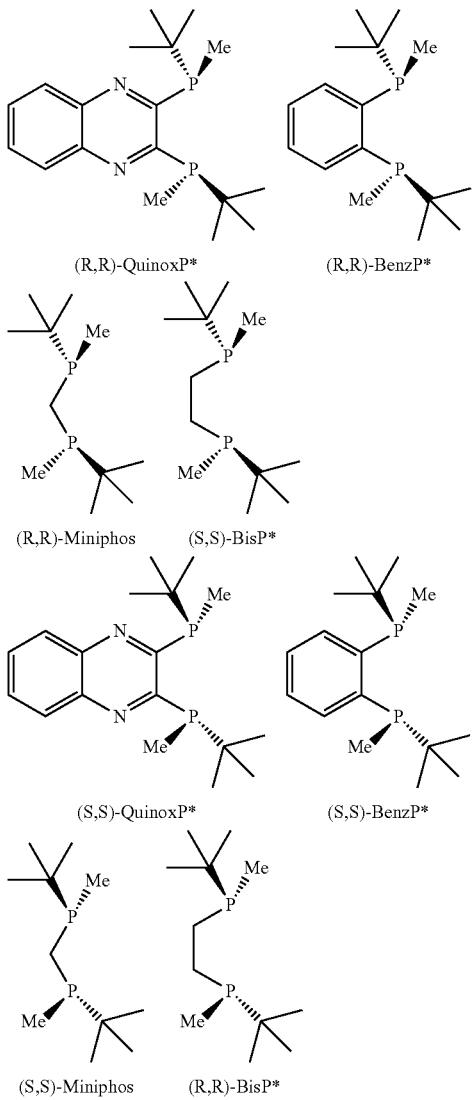

L' is any one auxiliary diene ligand selected from the group consisting of 1,5-cyclooctadiene (referred to as "cod" for abbreviation) and 2,5-norbornadiene (referred to as "nbd" for abbreviation). X is any one anion selected from the group consisting of $SbF_6^-$ and $BF_4^-$.

In the present method for preparing a chiral γ-secondary amino alcohol, preferably, the diphosphine-rhodium complex and the acid addition salt of β-secondary amino ketone represented by the general formula (1) are in a molar ratio of 1/200~1/20000.

In the present method for preparing a chiral γ-secondary amino alcohol, preferably, the metal salt additive is any one selected from the group consisting of zinc acetate, cerium chloride, zinc trifluoromethane sulfonate, copper chloride, copper acetate, zinc iodide, copper iodide, zinc chloride, magnesium sulfate, ferric chloride and aluminum chloride.

In the present method for preparing a chiral γ-secondary amino alcohol, preferably, the alkali is any one selected from the group consisting of potassium hydroxide, sodium hydroxide, potassium carbonate, sodium carbonate, cesium carbonate, potassium bicarbonate, sodium bicarbonate, potassium phosphate, dipotassium phosphate, monopotassium phosphate, triethylamine, sodium acetate and potassium tert-butoxide.

In the present method for preparing a chiral γ-secondary amino alcohol, preferably, the solvent is a polar solvent. More preferably, the solvent is any one or two or more of those selected from the group consisting of ethyl acetate, methylene chloride, tetrahydrofuran, methanol, ethanol, isopropanol and trifluoroethanol.

In the present method for preparing a chiral γ-secondary amino alcohol, preferably, the pressure of hydrogen is 10~100 bar in the hydrogen atmosphere, the reaction temperature is −20~100° C., and the reaction time is 1~48 hours.

DETAILED EMBODIMENTS

The method for preparing a chiral γ-secondary amino alcohol in the present invention can be represented by the following reaction scheme.

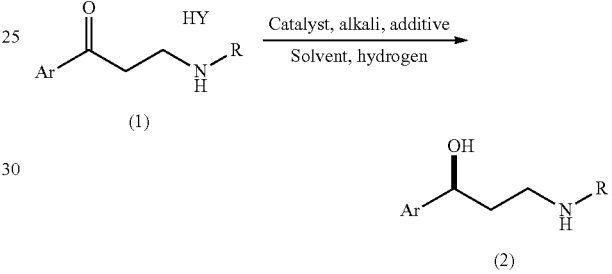

In the present method for preparing a γ-secondary amino alcohol compound, in the general formulas (1) and (2), Ar and R are not changed after the reaction.

In the general formula (1), HY represents an acid. As an acid represented by HY, various acids that can form an acid addition salt with a secondary amino group may be used, such as, hydrochloric acid, sulfuric acid, phosphoric acid, tartaric acid, p-methylbenzenesulfonic acid, trifluoromethanesulfonic acid, salicylic acid, tetrafluoroboric acid, hexafluorophosphoric acid, hexafluoroantimonic acid or the like. In other words, in the present preparation method, hydrochloride, sulfate, phosphate, tartrate, p-toluenesulfonate, trifluoromethanesulfonate, salicylate, tetrafluoroborate, hexafluorophosphate, hexafluoroantimonate or the like may be used as the acid addition salt of β-secondary amino ketone represented by the general formula (1).

In the general formulas (1) and (2), Ar is an aryl group with or without substituent group(s). As the aryl group, among many others, phenyl, naphthyl, and heterocyclic aryl, such as, furyl and thienyl, may be exemplified. In addition, as a substituent group in those aryl groups, alkyl, alkoxy, halogen, halogenated alkyl may be exemplified. The number of those substituent groups in the aryl group may be one or two or more. In addition, those substituent groups in the aryl group may form a ring. As detailed examples of Ar in the present invention, those as follows may be exemplified: phenyl, 2-methyl phenyl, 3-methyl phenyl, 4-methyl phenyl, 2-methoxy phenyl, 3-methoxy phenyl, 4-methoxy phenyl, 2-ethoxy phenyl, 3-ethoxy phenyl, 4-ethoxy phenyl, 2-fluoro phenyl, 3-fluoro phenyl, 4-fluoro phenyl, 2-chloro phenyl, 3-chloro phenyl, 4-chloro phenyl, 2-bromo phenyl, 3-bromo phenyl, 4-bromo phenyl, 2-iodo phenyl, 3-iodo phenyl, 4-iodo phenyl, 1-naphthyl, 2-naphthyl, 2-trifluoromethyl phenyl, 3-trifluoromethyl phenyl, 4-trifluoromethyl phenyl, 2-furyl, 2-thienyl, 3,4-dimethoxy phenyl. 3,4-dimethyl phenyl, 3,4-dichloro phenyl and 3,4-methylenedioxy phenyl (i.e., Ar=3,4-OCH$_2$OC$_6$H$_3$—) or the like.

In the general formulas (1) and (2), R represents an alkyl group or an aralkyl group, preferably, a linear or branched alkyl or aralkyl group having a carbon atom number of 1~8, and more preferably, a linear or branched alkyl having a carbon atom number of 1~4. As detailed examples of R, those as follows can be exemplified: methyl, ethyl, propyl, iso-propyl, butyl, iso-butyl, tert-butyl, pentyl, iso-pentyl, neo-pentyl, hexyl, heptyl, octyl, benzyl or the like.

In the present preparation method, the diphosphine-rhodium complex of [Rh(L)(L')]X serves as the catalyst. Amone many others, L is any one chiral diphosphine ligand selected from the group consisting of (R,R)-QuinoxP*, (R,R)-BenzP*, (R,R)-Miniphos, (S,S)-BisP*, (S,S)-QuinoxP*, (S,S)-BenzP*, (S,S)-Miniphos and (R,R)-BisP* as follows,

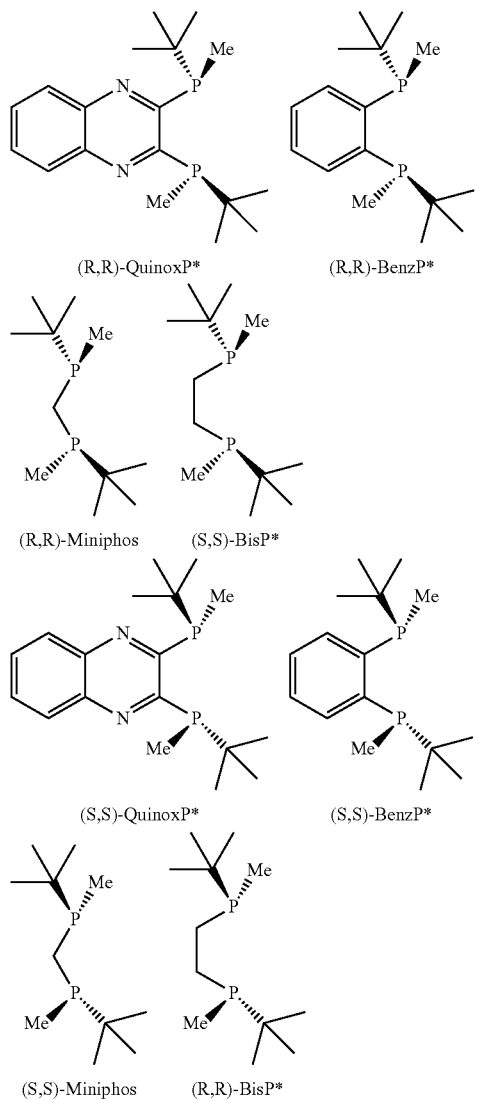

(R,R)-QuinoxP*    (R,R)-BenzP*

(R,R)-Miniphos    (S,S)-BisP*

(S,S)-QuinoxP*    (S,S)-BenzP*

(S,S)-Miniphos    (R,R)-BisP*

L' is any one auxiliary diene ligand selected from the group consisting of 1,5-cyclooctadiene (referred to as "cod" for abbreviation) and 2,5-norbornadiene (referred to as "nbd" for abbreviation). X is any one anion selected from the group consisting of SbF$_6^-$ and BF$_4^-$.

In the preparation method, the alkali is not specifically limited, as long as the alkali is well-know in the art, and it allows the catalytic asymmetric hydrogenation of the present invention to be carried out. However, in view of cost and commercial availability in practice, the alkali used in the present invention is preferably potassium hydroxide, sodium hydroxide, potassium carbonate, sodium carbonate, cesium carbonate, potassium bicarbonate, sodium bicarbonate, potassium phosphate, dipotassium phosphate, monopotassium phosphate, triethylamine, sodium acetate, potassium tert-butoxide or the like.

In the present preparation method, the hydrogen pressure in the hydrogen atmosphere is not specifically limited, as long as the catalytic asymmetric hydrogenation of the present invention can be carried out. However, in view of the reaction yield and reaction efficiency, the hydrogen pressure in the hydrogen atmosphere is set to 10~100 bar, preferably, 20~80 bar, and more preferably, 20~50 bar.

In the present preparation method, the solvent is not specifically limited, as long as raw materials of the reaction can be dissolved in the solvent, and the catalytic asymmetric hydrogenation of the present invention can be carried out. However, in view of the reaction yield and reaction efficiency, the solvent is preferably a polar solvent. Among many others, the solvent is preferably one or two or more of those selected from ethyl acetate, methylene chloride, tetrahydrofuran, methanol, ethanol, isopropanol and trifluoroethanol. There is no specific limitation for the mixed solvent of two or more solvents, as long as the types of solvents and ratio thereof are suitably chosen as required.

The present preparation method can be carried out by the means of mixing. The mixing rate is not specifically limited, as long as the reaction of the present invention can be carried out.

In the present preparation method, the reaction temperature and reaction time are not specifically limited, as long as the reaction of the present invention can be carried out. However, in view of the reaction yield and reaction efficiency, the reaction temperature can be set to −20~100° C., preferably, 0~50° C., more preferably, 25~50° C., and still more preferably, 25~30° C. Further, the reaction time can be set to 1~48 hours, preferably, 1~24 hours, more preferably, 6~24 hours, and still more preferably, 12~24 hours.

In the present preparation method, the metal salt additive is any one selected from the group consisting of zinc acetate, cerium chloride, zinc trifluoromethane sulfonate, copper chloride, copper acetate, zinc iodide, copper iodide, zinc chloride, magnesium sulfate, ferric chloride and aluminum chloride.

In the present preparation method, preferably, the molar ratio of the acid addition salt of β-secondary amino ketone represented by the general formula (1): the alkali:the metal salt additive is 1:(0.5~2.0):(0.1~2.0), preferably, 1:(0.5~2.0):(0.1~1.0), more preferably, 1:(0.5~1.0):(0.5~1.0), and especially preferably, 1:1:1.

In the present preparation method, preferably, the molar ratio of the diphosphine ligand-rhodium complex/the acid addition salt of β-secondary amino ketone of the general formula (1) is 1/200~1/20000, preferably, 1/500~1/20000, more preferably, 1/1000~1/20000, still more preferably, 1/2000~1/20000, and especially preferably, 1/10000~1/20000.

The major configuration of the compound of γ-secondary amino alcohol as the product obtained according to the present preparation method is determined by the configuration of the catalyst used in the preparation (i. e., the diphosphine ligand-rhodium complex). In other words, in a situation that the configuration of the catalyst is defined, the main configuration of the product obtained according to the present preparation method is also decided. The product obtained according to the present preparation method (i. e., the chiral γ-secondary amino alcohol represented by the general formula (2)) has a major configuration of R or S configuration.

As compared to the methods for preparation of chiral γ-secondary amino alcohol in the prior art, the present preparation method have several advantages. Specifically, the reaction condition is mild; the post-treatment is simplified; the chiral catalyst can be easily synthesized, and is stable in properties; the substrate can be widely applied; and the yield of the product can be increased considerably. Especially, as compared to the preparation methods using catalyst alone without adding the metal salt additive, the yield of the product can be increased considerably in the present preparation method. In addition, according to the present preparation method, the product can has an enantiomeric excess as high as 99%, and have a high optical purity. The present invention provides a feasible process for industrialized production of the chiral γ-secondary amino alcohol.

EXAMPLES

Detailed examples for the present preparation method are given as follows. Clearly, the protection scope of the present invention is not limited to the following examples.

In the following examples, the substrates (i.e., the acid addition salt of β-secondary amino ketone represented by the general formula (1)) are shown as 1a, 1b, 1c, 1d, 1e, 1f, 1g, 1h, 1i, 1j, 1k, 1l, 1m, 1n, 1o and 1p. Correspondingly, the products (i.e., the compound of γ-secondary amino alcohol represented by the general formula (2)) are shown as 2a, 2b, 2c, 2d, 2e, 2f, 2g, 2h, 2i, 2j, 2k, 2l, 2m, 2n, 2o and 2p.

In addition, in the following examples, the value of yield is calculated according to the following equation.

$$\text{yield \%} = \frac{\text{mass of product actually obtained by separation}}{\text{mass of product calculated theoretically}} * 100\%$$

In addition, the theoretical enantiometri excess in percent (referred to as "ee value" for abbreviation hereinafter) is calculated according to the following equation.

enantiometri excess value % = {|[S]−[R]|/ ([S]+[R])}*100%

In the above equation, [S] represents the amount of S-configuration enantiomer in the product, and [R] represents the amount of R-configuration enantiomer in the product.

In the following examples, the enantiometri excess value was determined by chiral HPLC (high performance liquid chromatography). HPLC analysis was performed on an instrument of LC-2010 manufactured by Shimadzu Corporation (Japan) equipped with a chiral chromatography column of Daicel chiralpak OD-H, Daicel Chiralpak AD-H or Daicel Chiralpak OJ-H manufactured by Daicel Corp. (Japan) under the working condition as follows: the mobile phase was n-hexane/iso-propanol (volumetric ratio)=90/ 10~97/3; the flow rate of the mobile phase was 0.5~1.2 mL/min; and the detection wavelength was 222 nm.

In addition, in the following examples, all the products synthesized were determined for hydrogen nuclear magnetic resonance spectrum ($^1$H-NMR) and carbon nuclear magnetic resonance spectrum ($^{13}$C-NMR) data. For compounds unreported in literatures, high resolution mass spectrum and infrared spectrum were determined.

In addition, in the following examples, each of the synthesized compounds was analyzed by NMR and HPLC. For the sake of simplicity, however, the data is shown specifically merely when the compound is mentioned for the first time, and is omitted afterwards for the same compound.

In the examples of the present invention, the NMR analysis was performed on an instrument of Mercury Plus-400 (400 MHz, $^1$H; 100 MHz, $^{13}$C) Spectrometer manufactured by the Varian Corporation. The high resolution mass spectrum was recorded on an instrument of Q-TOF Premier manufactured by Waters Corporation (U.S.). The infrared spectrum was recorded on an instrument of PerkinElmer Spectrum 100 FT-IR Spectrometer. Specific optical rotation was determed on in instrument of Rudolph Research Analytical Autopol VI Automatic Polarimeter (using a detection wavelength of 589 nm and an optical path length of 50 mm).

Example 1

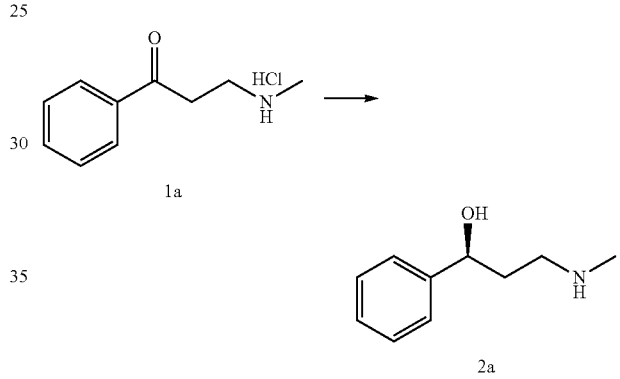

Into a 50 mL reaction vial, 1.5 mg of [Rh((S,S)-BenzP*) (cod)]SbF$_6$ as a catalyst, 803 mg of N-methyl-3-carbonyl-3-phenyl propylamine hydrochloride (substrate 1a), 277 mg of potassium carbonate, and 241 mg of magnesium sulfate [ketone:catalyst:alkali:additive=2000:1:1000:1000 (molar ratio)] were added separately. The reaction vial was placed into a hydrogenation autoclave, and was ventilated with hydrogen gas by vacuum-pumping for 3 times. 2 mL of degassed ethyl acetate was added under protection of hydrogen gas. Finally the hydrogen pressure was set to 50 bar. The reaction mixture was vigorously stirred for 1 hour at the temperature of 50° C. After the reaction was terminated, the mixture was concentrated by distillation to remove the solvent. The residue was subjected to column chromatography using alkaline alumina (methylene chloride VI/methanol V2=20/l) to give a product 2a as pale yellow oil. The yield of the product 2a was 80%.

The analysis data of the product 2a was as follows.

$^1$H-NMR (400 MHz, CDCl$_3$) δ 7.38-7.31(m, 4H), 7.26-7.21(m, 1H), 4.93(dd, J=3.2 Hz, 8.4 Hz, 1H), 3.04(br s, 2H), 2.92-2.81(m, 2H), 2.44(s, 3H), 1.91-1.73(m, 2H;

$^{13}$C-NMR (100 MHz, CDCl$_3$) δ 145.4, 128.4, 127.1, 125.8, 75.6, 50.6, 37.3, 36.3.

The amine group in the product 2a was acetylated to give the following compound 3a. The ee value of 3a was 92% as determined by chiral HPLC. Accordingly, the product 2a had an ee value of 92%.

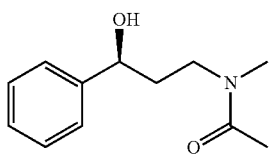

3a

The HPLC analysis was carried out under the condition as follows. A chiral chromatography column of Daicel chiralpak OD-H manufactured by Daicel Corp. (Japan) was used. The mobile phase was n-hexane/iso-propanol (volumetric ratio)=95:5. The flow rate of the mobile phase was 1.0 mL/min, $t_{major}$=44.0 min, $t_{minor}$=66.3 min.

The NMR data of the compound 3a was as follows.

$^1$H-NMR (400 MHz, CDCl$_3$) δ 7.37(m, 5H), 4.67(t, J=6.4 Hz, 0.2H), 4.54(d, J=7.2 Hz, 0.8H), 4.53(br s, 1H), 4.10-4.03(m, 0.8H), 3.50-3.34(m, 0.4H), 3.13-3.07(m, 0.8H), 2.99(s, 2.3H), 2.89(s, 0.7H), 2.08(s, 2.3H), 2.06(s, 0.7H), 1.94-1.90(m, 1H), 1.85-1.77(m, 1H);

$^{13}$C-NMR (100 MHz, CDCl$_3$) δ 172.3, 144.2, 128.9, 128.5, 128.1, 127.3, 125.8, 71.6, 70.1, 47.6, 44.8, 37.5, 36.9, 36.5, 33.3, 21.8, 21.4.

Example 2

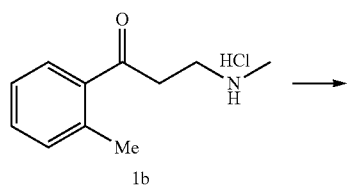

1b

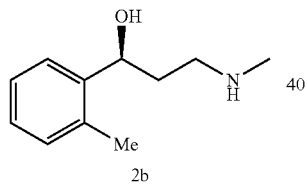

2b

Into a 50 mL reaction vial, 1.5 mg of [Rh((S,S)-BenzP*)(cod)]SbF$_6$ as a catalyst, 85.5 mg of N-methyl-3-carbonyl-3-(2-methyl phenyl)propylamine hydrochloride (substrate 1b), 21.2 mg of sodium carbonate, and 73.4 mg of zinc acetate [ketone:catalyst:alkali:additive=200:1:100:200 (molar ratio)] were added separately. The reaction vial was placed into a hydrogenation autoclave, and was ventilated with hydrogen gas by vacuum-pumping for 3 times. 2 mL of degassed ethyl acetate was added under protection of hydrogen gas. Finally the hydrogen pressure was finally adjusted to 50 bar. The reaction mixture was vigorously stirred for 24 hour at the temperature of −20° C. After the reaction was terminated, the mixture was concentrated by distillation to remove the solvent. The residue was subjected to column chromatography using alkaline alumina (methylene chloride V1/methanol V2=20/1) to give a product 2b as pale yellow oil . The yield of the product 2b was 75%.

The analysis data of the product 2b was as follows.

$^1$H-NMR (400 MHz, CDCl$_3$) δ 7.55(d, J=7.6 Hz, 1H), 7.22(t, J=7.2 Hz, 1H), 7.14(td, J=1.2 Hz, 7.6 Hz, 1H), 7.10(d, J=7.6 Hz, 1H), 5.13(dd, J=3.2 Hz, 8.8 Hz, 1H), 3.15(br s, 2H), 2.96-2.83(m, 2H), 2.46(s, 3H), 2.30(s, 3H), 1.87-1.81(m, 1H), 1.76-1.67(m, 1H);

$^{13}$C-NMR (100 MHz, CDCl$_3$) δ 143.1, 134.1, 130.4, 127.0, 126.3, 125.7, 72.3, 50.8, 36.2, 35.4, 19.2.

The amine group in the product 2b was acetylated to give the following compound 3b. The ee value of 3b was 90% as determined by chiral HPLC. Accordingly, the product 2b had an ee value of 90%.

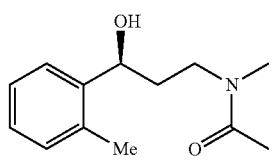

3b

The HPLC analysis was carried out under the condition as follows. A chiral chromatography column of Daicel chiralpak OD-H manufactured by Daicel Corp. (Japan) was used. The mobile phase was n-hexane/iso-propanol (volumetric ratio)=90:10. The flow rate of the mobile phase was 1.0 mL/min, $t_{major}$=13.6 min, $t_{minor}$=25.6 min.

The NMR data of the compound 3b was as follows.

$^1$H-NMR (400 MHz, CDCl3) δ 7.51(d, J=7.2 Hz, 0.8H), 7.47(d, J=7.2 Hz, 0.2H), 7.21(td, J=1.2 Hz, 7.6 Hz, 1H), 7.18-7.09(m, 2H), 4.92(dd, J=4.0 Hz, 8.8 Hz, 0.2H), 4.72(dd, J=2.4 Hz, 10.4 Hz, 0.8H), 4.33(br s, 1H), 4.24-4.16(m, 0.8H), 3.59-3.51(m, 0.2H), 3.46-3.39(m, 0.2H), 3.07-3.00(m, 0.8H), 3.04(s, 2.3H), 2.92(s, 0.7H), 2.31(s, 0.7H), 2.28(s, 2.3H), 2.75(s, 2.3H), 2.10(s, 0.7H), 1.93-1.85(m, 1H), 1.75-1.67(m, 1H);

$^{13}$C-NMR (100 MHz, CDCl3) δ 172.3, 171.1, 142.2, 134.0, 130.8, 130.4, 127.8, 127.2, 126.7, 126.5, 125.4, 125.1, 67.9, 66.7, 47.8, 45.0, 36.5, 36.2, 35.7, 33.4, 21.8, 21.4, 19.2.

Example 3

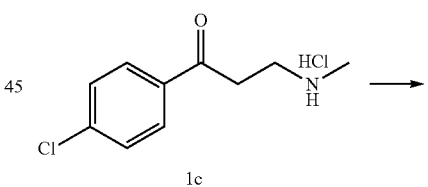

1c

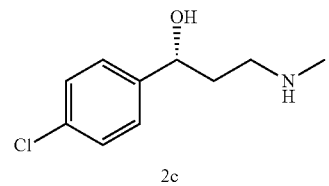

2c

Into a 50 mL reaction vial, 1.5 mg of [Rh((R,R)-QuinoxP*)(cod)]SbF$_6$ as a catalyst, 93.6 mg of N-methyl-3-carbonyl-3-(4-chloro phenyl)propylamine hydrochloride (substrate 1c), 22.4 mg of potassium hydroxide, and 145.4 mg of zinc trifluoromethane sulfonate [ketone:catalyst:alkali:additive=200:1:200:200 (molar ratio)] were added separately. The reaction vial was placed into a hydrogenation autoclave, and was ventilated with hydrogen gas by vacuum-pumping for 3 times. 2 mL of degassed ethanol was added under protection of hydrogen gas. Finally the hydrogen pressure was adjusted to 50 bar. The reaction mixture was vigorously stirred for 12 hour at the temperature of 0° C. After the reaction was terminated, the mixture was concentrated by distillation to remove the solvent. The residue was subjected to column chromatography using alkaline alumina (methylene chloride V1/methanol V2=20/ l) to give a product 2c as pale yellow solid. The yield of the product 2c was 82%.

The NMR data of the product 2c was as follows.

$^1$H-NMR (400 MHz, CDCl$_3$) δ 7.31(s, 4H), 4.92(dd, J=3.2 Hz, 8.8 Hz, 1H), 3.84 (br s, 2H), 2.91-2.82(m, 2H), 2.44(s, 3H), 1.88-1.83(m, 1H), 1.71-1.68(m, 1H);

$^{13}$C-NMR (100 MHz, CDCl$_3$) δ 144.0, 132.7, 128.5, 127.3, 75.3, 50.6, 37.0, 36.3.

The amine group in the product 2c was acetylated to give the following compound 3c. The ee value of 3c was 94% as determined by chiral HPLC. Accordingly, the product 2c had an ee value of 94%.

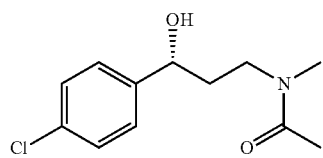

3c

The HPLC analysis was carried our under the condition as follows. A chiral chromatography column of Daicel chiralpak OD-H manufactured by Daicel Corp. (Japan) was used. The mobile phase was n-hexane/iso-propanol (volumetric ratio)=95:5. The flow rate of the mobile phase was 1.0 mL/min, t$_{minor}$=36.3 min, t$_{major}$=42.4 min.

The NMR data of the compound 3c was as follows.

$^1$H-NMR (400 MHz, CDCl$_3$) δ 7.21(s, 4H) 4.87(br s, 1H), 4.54(t, J=6.4 Hz, 0.3H), 4.44(dd, J=3.2 Hz, 10.4 Hz, 0.7H), 3.91-3.84(m, 0.8H), 3.42~3.24 (m, 0.4H), 3.073.03 (m, 0.8H), 2.92 (s, 2.1H), 2.79 (s, 0.9H), 1.99 (s, 2.1H), 1.97 (s, 0.9H), 1.84-1.79 (m, 1H), 1.72-1.63 (m, 1H);

$^{13}$C-NMR (100 MHz, CDCl$_3$) δ 172.3, 171.2, 143.4, 142.9, 133.2, 132.8, 128.7, 128.5, 127.3, 70.4, 69.6, 47.6, 44.8, 37.5, 36.8, 36.6, 33.3, 21.8, 21.3.

Example 4

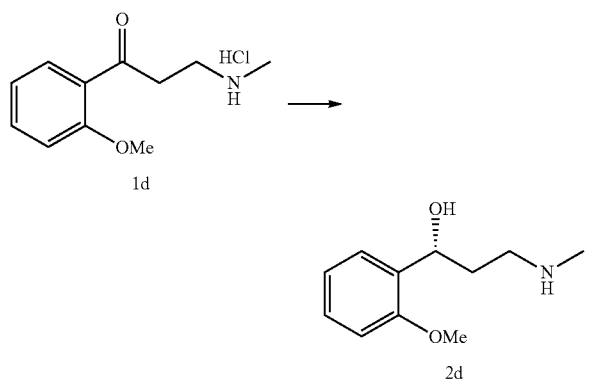

Into a 50 mL reaction vial, 1.5 mg of [Rh((R,R)-Minphos) (cod)]SbF$_6$ as a catalyst, 919 mg of N-methyl-3-carbonyl-3-(2-methoxy phenyl)propylamine hydrochloride (substrate 1d), 801 mg of potassium hydroxide, and 799 mg of copper acetate [ketone:catalyst:alkali:additive=2000:1:4000:2000 (molar ratio)] were added separately. The reaction vial was placed into a hydrogenation autoclave, and was ventilated with hydrogen gas by vacuum-pumping for 3 times. 15 mL of degassed methylene chloride was added under protection of hydrogen gas. Finally the hydrogen pressure was adjusted to 10 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/l) to give a product 2d as pale yellow oil. The yield of the product 2d was 78%.

The analysis data of the product 2d was as follows.

$^1$H-NMR (400 MHz, CDCl$_3$) δ 7.25(d, J=8.8 Hz, 1H), 6.96(s, 1H), 6.93(d, J=7.6 Hz, 1H), 6.78(dd, J=2.0 Hz, 8.0 Hz, 1H), 4.91(dd, J=3.2 Hz, 8.4 Hz, 1H), 3.81(s, 3H), 2.98(br s, 2H), 2.93-2.81(m, 2H), 2.44(s, 3H), 1.92-1.85(m, 1H), 1.81-1.72(m, 1H);

$^{13}$C-NMR (100 MHz, CDCl$_3$) δ 159.9, 147.0, 129.4, 118.2, 112.7, 111.3, 75.6, 55.4, 50.6, 37.0, 36.2;

IR (KBr, v/cm$^{-1}$): 3307, 2943, 2908, 2835, 2800, 1601, 1487, 1259, 1155, 1043, 871, 784, 700;

HRMS (ESI-MS): C$_{11}$H$_{18}$NO$_2$ [M+H]$^+$ theoretically calculated: 196.1338, obtained: 196.1346

The amine group in the product 2d was acetylated to give the following compound 3d. The ee value of 3d was 88% as determined by chiral HPLC. Accordingly, the product 2d had an ee value of 88%.

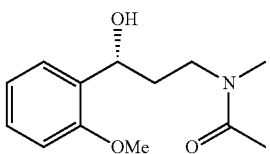

3d

The HPLC analysis was carried out under the condition as follows. A chiral chromatography column of Daicel chiralpak AD-H manufactured by Daicel Corp. (Japan) was used. The mobile phase was n-hexane/iso-propanol (volumetric ratio)=95:5. The flow rate of the mobile phase was 1.0 mL/min, t$_{minor}$=58.5 min, t$_{major}$=64.4 min.

The NMR data of the compound 3d was as follows.

$^1$H-NMR (400 MHz, CDCl$_3$) δ 7.46(dd, J=1.6 Hz, 7.2 Hz, 0.6H), 7.33(dd, J=1.6 Hz, 7.6 Hz, 0.4H), 7.26-7.18(m, 1H), 6.95(t, J=7.2 Hz, 1H), 6.86(d, J=8.4 Hz, 0.4H), 6.82 (d, J=8.4 Hz, 0.6H), 4.89(dd, J=3.2 Hz, 8.8 Hz, 0.4H), 4.81(dd, J=2.4 Hz, 10.0 Hz, 0.6H), 4.29(br s, 1H), 4.11-4.02 (m, 0.8H), 3.82(s, 1.1H), 3.80(s, 1.9H), 3.55-3.35(m, 0.5H), 3.11-3.05(m, 0.8H), 3.00(s, 1.9H), 2.89(s, 1.9H), 2.10(s, 1.9H), 2.08(s, 1.1H), 2.05-1.91(m, 1H), 1.72-1.63(m, 1H);

$^{13}$C-NMR (100 MHz, CDCl$_3$) δ 172.1, 171.1, 156.4, 155.9, 132.5, 132.2, 128.8, 128.1, 126.5, 126.5, 121.0, 110.6, 110.3, 67.4, 65.6, 55.5, 47.9, 44.9, 36.3, 35.6, 35.0, 33.2, 21.9, 21.4.

Example 5

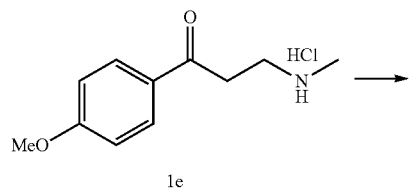

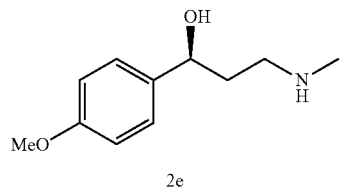

Into a 50 mL reaction vial, 1.5 mg of [Rh((R,R)-BisP*)(cod)]BF$_4$ as a catalyst, 91.9 mg of N-methyl-3-carbonyl-3-(4-methoxy phenyl)propylamine hydrochloride (substrate 1e), 80.1 mg of potassium phosphate, and 79.9 mg of zinc chloride [ketone:catalyst:alkali:additive=200:1:400:200 (molar ratio)] were added separately. The reaction vial was placed into a hydrogenation autoclave, and was ventilated with hydrogen gas by vacuum-pumping for 3 times. 2 mL of degassed methanol was added under protection of hydrogen gas. Finally the hydrogen pressure was adjusted to 100 bar, and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2e as white solid. The yield of the product 2e was 87%.

The analysis data of the product 2e was as follows.

$^1$H-NMR (400 MHz, CDCl$_3$) δ 7.23(d, J=8.8 Hz, 2H), 6.82(d, J=8.8 Hz, 2H), 4.76(dd, J=4.0 Hz, 8.0 Hz, 1H), 3.77(br s, 2H), 3.74(s, 3H), 2.78-2.67(m, 2H), 2.33(s, 3H), 1.78-1.67(m, 2H);

$^{13}$C-NMR (100 MHz, CDCl$_3$) δ 158.8, 137.7, 127.0, 113.8, 74.7, 55.4, 50.3, 37.5, 36.2.

The amine group in the product 2e was acetylated to give the following compound 3e. The ee value of 3e was 96% as determined by chiral HPLC. Accordingly, the product 2e had an ee value of 96%.

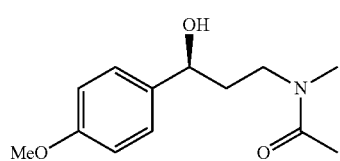

The HPLC analysis was carried out under the condition as follows. A chiral chromatography column of Daicel chiralpak OD-H manufactured by Daicel Corp. (Japan) was used. The mobile phase was n-hexane/iso-propanol (volumetric ratio)=90:10. The flow rate of the mobile phase was 1.0 mL/min, $t_{major}$=27.7 min, $t_{minor}$=33.0 min.

The NMR data of the compound 3e was as follows.

$^1$H-NMR (400 MHz, CDCl$_3$) δ 7.28-7.23(m, 2H), 6.88-6.83(m, 2H), 4.59(dd, J=4.8 Hz, 8.4 Hz, 0.3H), 4.48(dd, J=3.6 Hz, 10.0 Hz, 0.7H), 4.41(br s, 1H), 4.04-3.97(m, 0.8H), 3.78(s, 0.8H), 3.77(s, 2.2H), 3.46-3.31(m, 0.4H), 3.12-3.06(m, 0.4H), 2.98(s, 2.2H), 2.87(s, 0.8H), 2.07(s, 2.2H), 2.04(s, 0.8H), 1.96-1.86(m, 1H), 1.83-1.75(m, 1H);

$^{13}$C-NMR (100 MHz, CDCl$_3$) δ 172.3, 171.1, 158.9, 136.4, 127.1, 114.2, 113.9, 71.2, 69.8, 55.5, 47.7, 44.9, 37.4, 36.8, 36.5, 33.3, 21.8, 21.4.

Example 6

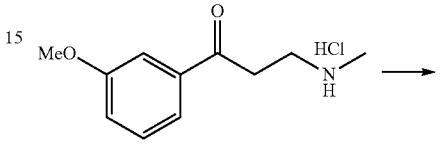

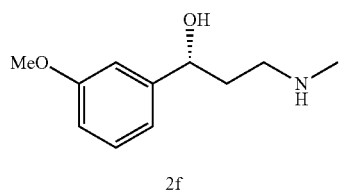

Into a 50 mL reaction vial, 1.5 mg of [Rh((S,S)-BisP*)(nbd)]BF4 as a catalyst, 919 mg of N-methyl-3-carbonyl-3-(3-methoxy phenyl)propylamine hydrochloride (substrate 1f), 1394 mg of dipotassium phosphate, and 682 mg of copper chloride [ketone:catalyst:alkali:additive=2000:1:4000:2000 (molar ratio)] were added separately. The reaction vial was placed into a hydrogenation autoclave, and was ventilated with hydrogen gas by vacuum-pumping for 3 times. 2 mL of degassed ethanol was added under protection of hydrogen gas. Finally the hydrogen pressure was adjusted to 20 bar, and the reaction mixture was vigorously stirred for 6 hour at the temperature of 100° C. After the reaction was terminated, the mixture was concentrated by distillation to remove the solvent. The residue was subjected to column chromatography using alkaline alumina (methylene chloride V1/methanol V2=20/1) to give a product 2f as pale yellow oil. The yield of the product 2f was 77%.

The analysis data of the product 2f was as follows.

$^1$H-NMR (400 MHz, CDCl$_3$) δ 7.25(d, J=8.8 Hz, 1H), 6.96(s, 1H), 6.93(d, J=7.6 Hz, 1H), 6.78(dd, J=2.0 Hz, 8.0 Hz, 1H), 4.91(dd, J=3.2 Hz, 8.4 Hz, 1H), 3.81(s, 3H), 2.98(br s, 2H), 2.93-2.81(m, 2H), 2.44(s, 3H), 1.92-1.85(m, 1H), 1.81-1.72(m, 1H); $^1$C-NMR (100 MHz, CDCl$_3$) δ 159.9, 147.0, 129.4, 118.2, 112.7, 111.3, 75.6, 55.4, 50.6, 37.0, 36.2;

IR (KBr, v/cm$^{-1}$): 3307, 2943, 2908, 2835, 2800, 1601, 1487, 1259, 1155, 1043, 871, 784, 700;

HRMS (ESI-MS): C$_{11}$H$_{18}$NO$_2$ [M+H]$^+$ theoretically calculated: 196.1338, obtained: 196.1346

The amine group in the product 2f was acetylated to give the following compound 3f. The ee value of 3f was 89% as determined by chiral HPLC. Accordingly, the product 2f had an ee value of 89%.

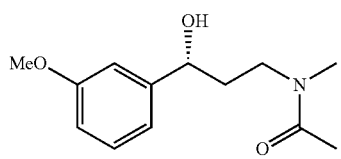

3f

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=90:10. The flow rate of the mobile phase was 1.0 mL/min, $t_{minor}$=27.4 min, $t_{major}$=33.1 min.

The analysis data of the compound 3f was as follows.

$^1$H-NMR (400 MHz, CDCl$_3$) δ 7.30-7.23(m, 1H), 6.97-6.91(m, 2H), 6.84(dd, J=2.4 Hz, 8.0 Hz, 0.3H), 6.80(dd, 2.4 Hz, 8.0 Hz, 0.7H), 4.66(t, J=6.4 Hz, 0.2H), 4.54(dd, J=3.2 Hz, 10.0 Hz, 0.8H), 4.11-4.04(m, 0.8H), 3.82(s, 3H), 3.53-3.35(m, 0.5H), 3.14-3.09(m, 0.8H), 3.01(s, 2.2H), 2.91 (s, 0.8H), 2.11(s, 2.2H), 2.09(s, 0.8H), 2.00-1.92(m, 1H), 1.86-1.78(m, 1H);

$^{13}$C-NMR (100 MHz, CDCl$_3$) δ 172.4, 171.2, 159.9, 146.2, 146.0, 130.0, 129.5, 118.2, 118.1, 113.4, 113.0, 111.5, 111.3, 71.5, 70.1, 55.5, 47.7, 44.8, 37.5, 36.9, 36.6, 33.4, 21.9, 21.4;

IR (KBr, v/cm$^{-1}$): 3373, 3002, 2940, 2836, 1621, 1488, 1455, 1435, 1362, 1259, 1156, 1042, 870, 786, 700, 609;

HRMS (ESI-MS): C$_{13}$H$_{20}$NO$_3$ [M+H]$^+$ calculated: 238.1443, obtained: 238.1443

Example 7

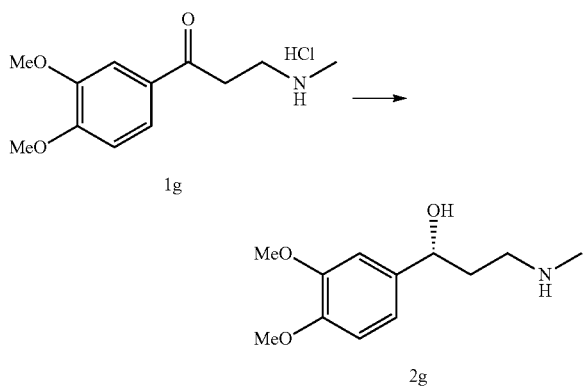

Into a 50 mL reaction vial, 1.5 mg of [Rh((S,S)-BisP*)(cod)]BF$_4$ as a catalyst, 103.9 mg of N-methyl-3-carbonyl-3-(3,4-dimethoxy phenyl)propylamine hydrochloride (substrate 1g), 108.9 mg of monopotassium phosphate, and 127.7 mg of copper iodide [ketone:catalyst:alkali:additive=200:1:400:200 (molar ratio)] were added separately. The reaction vial was placed into a hydrogenation autoclave, and was ventilated with hydrogen gas by vacuum-pumping for 3 times. 2 mL of degassed trifluoroethanol was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2g as white solid. The yield of the product 2g was 85%.

The analysis data of the product 2g was as follows.

$^1$H-NMR (400 MHz, CDCl$_3$) δ 6.94(s, 1H), 6.86-6.79(m, 2H), 4.85(dd, J=3.2 Hz, 8.4 Hz, 1H), 3.86(s, 3H), 3.84(s, 3H), 3.28(br s, 2H), 2.93-2.82 (m, 2H), 2.45(s, 3H), 1.90-1.81(m, 2H);

$^{13}$C-NMR (100 MHz, CDCl$_3$) δ 149.1, 148.2, 137.8, 117.9, 111.2, 109.2, 74.8, 56.1, 56.1, 50.1, 36.8, 35.8;

IR (KBr, v/cm$^{-1}$): 3430, 2939, 2837, 1593, 1516, 1464, 1417, 1262, 1234, 1139, 1075, 858, 812, 763;

HRMS (ESI-MS): C$_{12}$H$_{20}$NO$_3$ [M+H]$^+$ theoretically calculated: 226.1443, obtained: 226.1448

The amine group in the product 2g was acetylated to give the following compound 3g. The ee value of 3g was 93% as determined by chiral HPLC. Accordingly, the product 2g had an ee value of 93%.

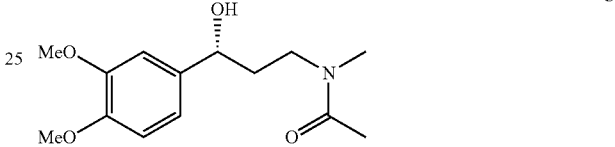

3g

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=90:10. The flow rate of the mobile phase was 1.0 mL/min, $t_{minor}$=49.7 min, $t_{major}$=65.2 min.

The analysis data of the compound 3g was as follows.

$^1$H-NMR (400 MHz, CDCl$_3$) δ 6.93(d, J=2.0 Hz, 0.8H), 6.86(d, J=1.6 Hz, 0.2H), 6.83-6.86(m, 2H), 4.56(dd, J=4.8 Hz, 8.4 Hz, 0.2H), 4.51(br s, 1H), 4.46(dd, J=3.2 Hz, 10.0 Hz, 0.8H), 4.02-3.95(m, 0.8H), 3.85-3.82(m, 6H), 3.45-3.30 (m, 0.4H), 3.11-3.05(m, 0.8H), 2.97(s, 2.2H), 2.86(s, 0.8H), 2.06(s, 2.2H), 2.03(s, 0.8H), 1.94-1.85(m, 1H), 1.82-1.74(m, 1H);

$^{13}$C-NMR (100 MHz, CDCl$_3$) δ 172.3, 171.1, 149.4, 149.1, 148.8, 148.3, 137.1, 137.0, 118.1, 118.0, 111.3, 111.1, 109.3, 109.0, 71.3, 70.0, 56.1, 56.1, 47.7, 44.9, 37.5, 36.9, 36.6, 33.3, 21.8, 21.3;

IR (KBr, v/cm$^{-1}$): 3420, 2936, 1621, 1516, 1456, 1417, 1263, 1234, 1139, 1025, 811, 763;

HRMS (ESI-MS): C$_{14}$H$_{21}$NO$_4$ [M+H]$^+$ theoretically calculated: 268.1549, obtained: 268.1547

Example 8

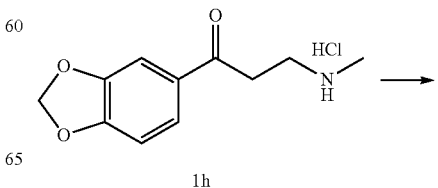

1h

-continued

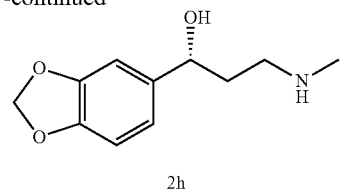

2h

Into a 50 mL reaction vial, 1.5 mg of [Rh((S,S)-BisP* (cod)]BF$_4$ as a catalyst, 975 mg of N-methyl-3-carbonyl-3-(3,4-methylenedioxy phenyl)propylamine hydrochloride (substrate 1h), 810 mg of triethylamine, and 649 mg of ferric chloride [ketone:catalyst:alkali:additive=2000:1:4000:2000 (molar ratio)] were added separately. The reaction vial was placed into a hydrogenation autoclave, and was ventilated with hydrogen gas by vacuum-pumping for 3 times. 15 mL of degassed iso-propanol was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2h as pale yellow oil. The yield of the product 2h was 89%.

The analysis data of the product 2h was as follows.

$^1$H-NMR (400 MHz, CDCl$_3$) δ 6.88(d, J=1.6 Hz, 1H), 6.80(dd, J=1.6 Hz, 8.0 Hz, 1H), 6.75(d, J=8.0 Hz, 1H), 5.93(s, 2H), 4.83(dd, J=3.2 Hz, 8.8 Hz, 1H), 3.28(br s, 2H), 2.90-2.82(m, 2H), 2.44(s, 3H), 1.84-1.69(m, 2H);

$^{13}$C-NMR (100 MHz, CDCl$_3$) δ 147.8, 146.6, 139.5, 119.0, 108.2, 106.6, 101.1, 75.5, 50.5, 37.1, 36.1;

IR (KBr, v/cm$^{-1}$): 3307, 2897, 1504, 1488, 1442, 1243, 1095, 1075, 1038, 932, 811;

HRMS (ESI-MS): C$_{11}$H$_{16}$NO$_3$ [M+H]$^+$ theoretically calculated: 210.1130, obtained: 210.1127

The amine group in the product 2h was acetylated to give the following compound 3h. The ee value of 3h was 94% as determined by chiral HPLC. Accordingly, the product 2h had an ee value of 94%.

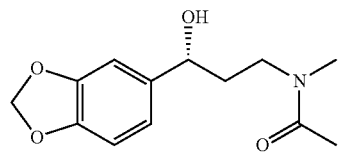

3h

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=90:10. The flow rate of the mobile phase was 1.0 mL/min, t$_{minor}$=29.4 min, t$_{major}$=34.2 min.

The analysis data of the compound 3h was as follows.

$^1$H-NMR (400 MHz, CDCl$_3$) δ 6.88(d, J=1.6 Hz, 0.7H), 6.84(s, 0.3H), 6.78(td, J=1.6 Hz, 8.0 Hz, 1H), 6.75(t, J=8.01 Hz, 1H), 5.94(s, 0.51H), 5.92(s, 1.5H), 4.58(dd, J=5.2 Hz, 8.0 Hz, 0.3H), 4.44(dd, J=3.2 Hz, 10.0 Hz, 0.7H), 4.42(br s, 1H), 4.09-4.01(m, 0.8H), 3.47-3.32(m, 0.5H), 3.08-3.03(m, 0.8H ), 3.00(s, 2.2H), 2.89(s, 0.8H), 2.10(s, 2.2H), 2.07(s, 0.8H), 1.94-1.84(m, 1H), 1.88-1.72(m, 1H);

$^{13}$-NMR (100 MHz, CDCl$_3$) δ 172.3, 171.1, 147.8, 146.8, 138.4, 119.2, 119.1, 108.5, 108.2, 106.6, 106.3, 101.3, 101.1, 71.5, 70.0, 47.7, 44.8, 37.5, 37.0, 36.5, 33.3, 21.8, 21.4;

IR (KBr, v/cm$^{-1}$): 3390, 2921, 1621, 1488, 1441, 1243, 1036, 931, 811;

HRMS (ESI-MS): C$_{13}$H$_{17}$NO$_4$Na [M+H]$^+$ theoretically calculated: 274.1055, obtained: 274.1050

Example 9

1i

2i

Into a 50 mL reaction vial, 1.5 mg of [Rh((R,R)-QuinoxP*)(cod)]SbF$_6$ as a catalyst, 1071 mg of N-methyl-3-carbonyl-3-(4-trifluoromethyl phenyl)propylamine hydrochloride (substrate 1i), 652 mg of cesium carbonate, and 107 mg of aluminum chloride [ketone:catalyst:alkali:additive=2000:1:1000:200 (molar ratio)] were added separately. The reaction vial was placed into a hydrogenation autoclave, and was ventilated with hydrogen gas by vacuum-pumping for 3 times. 4 mL of degassed tetrahydrofuran was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2i as white solid. The yield of the product 2i was 87%.

The analysis data of the product 2i was as follows.

$^1$H-NMR (400 MHz, CDCl$_3$) δ 7.60(d, J=8.0 Hz, 2H), 7.51 (d, J=8.8 Hz, 2H), 5.02(dd, J=2.8 Hz, 8.8 Hz, 1H), 3.85 (br s, 2H), 2.96-2.86(m, 2H), 2.47(s, 3H), 1.94-1.87(m, 1H), 1.79-1.69(m, 1H);

$^{13}$C-NMR (100 MHz, CDCl$_3$) δ 149.2, 129.5, 129.2, 128.9, 128.6, 128.4, 125.9, 125.7, 125.2, 125.2, 125.1, 125.1, 123.0, 120.3, 75.2, 50.4, 36.5, 36.0;

IR (KBr, v/cm$^{-1}$): 3282, 3105, 2935, 2899, 2816, 1618, 1482, 1422, 1332, 1162, 1115, 1068, 1053, 1015, 984, 851, 826;

HRMS (ESI-MS): C$_{11}$H$_{15}$NOF$_3$ [M+H]$^+$ theoretically calculated: 234.1106, obtained: 234.1199

The amine group in the product 2i was acetylated to give the following compound 3i. The ee value of 3i was 91% as determined by chiral HPLC. Accordingly, the product 2i had an ee value of 91%.

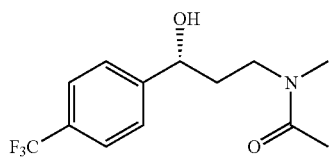

3i

The HPLC analysis was carried out under the condition as follows. A chiral chromatography column of Daicel chiralpak OJ-H manufactured by Daicel Corp. (Japan) was used. The mobile phase was n-hexane:iso-propanol (volumetric ratio)=95:5. The flow rate of the mobile phase was 1.0 mL/min, $t_{minor}$=10.0 min, $t_{major}$=11.8 min.

The analysis data of the compound 3i was as follows.

$^1$H-NMR (400 MHz, CDCl$_3$) δ 7.62-7.57(m, 2H), 7.50-7.45(m, 2H), 4.98(br s, 1H), 4.74(dd, J=4.4 Hz, 8.4 Hz, 0.1H), 4.59(dd, J=2.4 Hz, 10.0 Hz, 0.9H), 4.16-4.09(m, 0.9H), 3.58-3.36(m, 0.2H), 3.12-3.06(m, 0.9H), 3.03(s, 2.7H), 2.91(s, 0.3H), 2.11(s, 2.7H), 2.10(s, 0.3H), 1.97-1.92 (m, 1H), 1.80-1.71(m, 1H);

$^{13}$C NMR (100 MHz, CDCl$_3$) δ 172.4, 170.9, 148.1, 129.3, 129.0, 128.7, 128.3, 125.9, 125.6, 125.5, 125.5, 125.2, 125.2, 125.2, 125.1, 122.9, 70.5, 69.2, 47.2, 44.5, 37.4, 36.8, 36.4, 33.1, 21.6, 21.1.

IR (KBr, v/cm$^{-1}$): 3360, 2926, 1621, 1057, 1403, 1362, 1219, 1157, 1072, 1014, 837;

HRMS (ESI-MS): C$_{13}$H$_{17}$NO$_2$F$_3$ [M+H]$^+$ theoretically calculated: 276.1211, obtained: 276.1211

Example 10

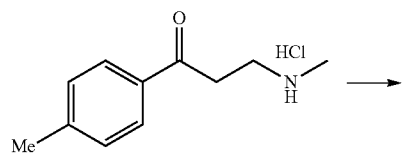

1j

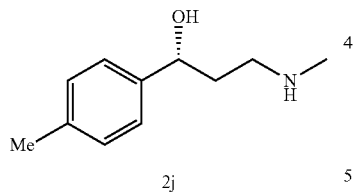

2j

Into a 50 mL reaction vial, 1.5 mg of [Rh((R,R)-QuinoxP*)(cod)]SbF$_6$ as a catalyst, 855 mg of N-methyl-3-carbonyl-3-(4-methyl phenyl)propylamine hydrochloride (substrate 1j), 160 mg of sodium hydroxide, and 493 mg of cerium chloride [ketone:catalyst:alkali:additive=2000:1:2000:1000 (molar ratio)] were added separately. The reaction vial was placed into a hydrogenation autoclave, and was ventilated with hydrogen gas by vacuum-pumping for 3 times. 10 mL of degassed tetrahydrofuran was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography rising alkaline alumina (methylene chloride V1/methanol V2=20/l) to give a product 2j as pale yellow oil. The yield of the product 2j was 87%.

The analysis data of the product 2j was as follows.

$^1$H-NMR (400 MHz, CDCl$_3$) δ 7.25(d, J=8.0 Hz, 2H), 7.14(d, J=7.6 Hz, 2H), 4.89(dd, J=3.6 Hz, 8.8 Hz, 1H), 3.02 (br s, 2H), 2.93-2.83(m, 2H), 2.45(s, 3H), 2.33(s, 3H), 1.91-1.75(m, 2H), 1.71-1.68(m, 1H);

$^{13}$C-NMR (100 MHz, CDCl$_3$) δ 142.2, 136.9, 129.1, 125.7, 75.4, 50.4, 36.9, 36.0, 21.3.

The amine group in the product 2j was acetylated to give the following compound 3j. The ee value of 3j was 96% as determined by chiral HPLC. Accordingly, the product 2j had an ee value of 96%.

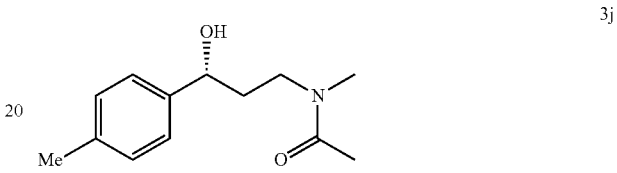

3j

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=95:5. The flow rate of the mobile phase was 1.0 mL/min, $t_{minor}$=41.1 min, $t_{major}$=55.7 min.

The analysis data of the compound 3j was as follows, $^1$H-NMR (400 MHz, CDCl$_3$) δ 7.22(t, J=8.0 Hz, 2H), 7.13(t, J=8.0 Hz, 2H), 4.61(dd, J=5.2 Hz, 7.6 Hz, 0.2H), 4.50(dd, J=3.6 Hz, 10.0 Hz, 0.8H), 4.44(br s, 1H), 4.04-3.97 (m, 0.8H), 3.47-3.31(m, 0.5H), 3.13-3.07(m, 0.8H), 2.97(s, 2.2H), 2.87(s, 0.8H), 2.33(s, 0.8H), 2.31(s, 2.2H), 2.07(s, 2.2H), 2.04(s, 0.8H), 1.96-1.87(m, 1H), 1.83-1.75(m, 1H);

$^{13}$C-NMR (100 MHz, CDCl$_3$) δ 172.3, 171.1, 141.4, 141.3, 137.7, 136.9. 129.9, 129.2, 125.8, 71.3, 70.1, 47.7, 44.8, 37.5, 36.9, 36.5, 33.3, 21.8, 21.3.

Example 11

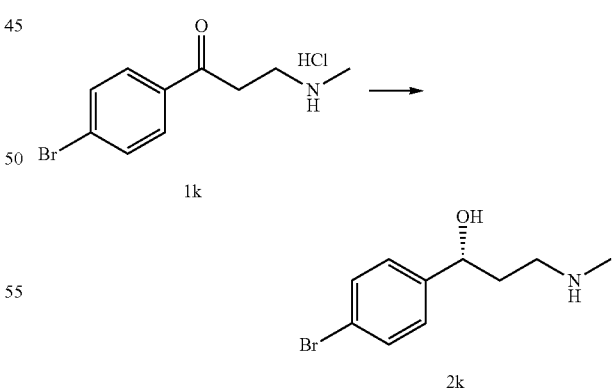

1k

2k

Into a 50 mL reaction vial, 1.5 mg of [Rh((R,R)-QuinoxP*)(cod)]SbF$_6$ as a catalyst, 111.4 mg of N-methyl-3-carbonyl-3-(4-bromo phenyl)propylamine hydrochloride (substrate 1k), 65.6 mg of sodium acetate, and 98.6 mg of cerium chloride [ketone:catalyst:alkali:additive=200:1:400:200 (molar ratio)] were added separately. The reaction vial was placed into a hydrogenation autoclave, and was ventilated with hydrogen gas by vacuum-pumping for 3 times, 2 mL of degassed tetrahydrofuran was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2k as white solid. The yield of the product 2k was 79%.

The analysis data of the product 2k was as follows.

$^1$H-NMR (400 MHz, CDCl$_3$) δ 7.47(d, J=8.4 Hz, 2H), 7.27(d, J=8.4 Hz, 2H), 4.91(dd, J=3.2 Hz, 8.4 Hz, 1H), 3.74 (br s, 2H), 2.91-2.86(m, 2H), 2.45(s, 3H), 1.89-1.82(m, 1H), 1.76-1.67(m, 1H);

$^{13}$C-NMR (100 MHz, CDCl$_3$) δ 144.3, 131.2, 127.4, 120.5, 75.1, 50.4, 36.7, 36.0.

The amine group in the product 2k was acetylated to give the following compound 3k. The ee value of 3k was 94% as determined by chiral HPLC. Accordingly, the product 2k had an ee value of 94%.

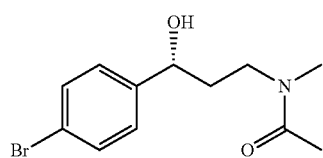

3k

The HPLC analysis was carried out under the condition as follows. A chiral chromatography column of Daicel chiralpak OD-H manufactured by Daicel Corp (Japan) was used. The mobile phase was n-hexane:iso-propanol (volumetric ratio)=95:5. The flow rate of the mobile phase was 1.0 mL/min, t$_{minor}$=36.7 min, t$_{major}$=41.3 min.

The analysis data of the compound 3k was as follows.

$^1$H-NMR (400 MHz, CDCl$_3$) δ 7.41-7.36(m, 2H) 7.19-7.13(m, 2H), 4.84(br s, 1H), 4.54(t, J=6.4 Hz, 0.2H), 4.43 (dd, J=3.2 Hz, 10.0 Hz, 0.8H), 3.96-3.89(m, 0.8H), 3.44-3.26(m, 0.5H), 3.08-3.02(m, 0.8H), 2.94(s, 2.2H), 2.81(s, 0.8H), 2.02 (s, 2.2H), 1.99(s, 0.8H), 1.89-1.81(m, 1H), 1.72-1.64(m, 1H);

$^{13}$C-NMR (100 MHz, CDCl$_3$) δ 172.4, 171.2, 143.9, 143.4, 131.7, 131.5, 127.7, 121.4, 120.9, 70.5, 69.6, 47.5, 44.8, 37.5, 36.8, 36.6, 33.3, 21.8, 21.3.

Example 12

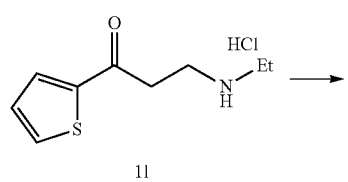

11

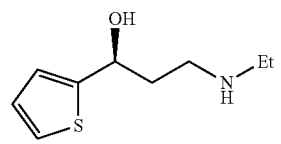

21

Into a 50 mL reaction vial, 1.5 mg of [Rh((S,S)-QuinoxP*)(cod)]SbF$_6$ as a catalyst, 219.1 mg of N-ethyl-3-carbonyl-3-(2-thienyl)propylamine hydrochloride (substrate 1l), 112.2 mg of potassium tert-butoxide, and 246.4 mg of cerium chloride [ketone:catalyst:alkali:additive=500:1:500:500 (molar ratio)] were added separately. The reaction vial was placed into a hydrogenation autoclave, and was ventilated with hydrogen gas by vacuum-pumping for 3 times. 5 mL of degassed tetrahydrofuran was added under protection of hydrogen gas. Finally the hydrogen pressure was adjusted to 20 bar and the reaction mixture was vigorously stirred for 12 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2l as white solid. The yield of the product 2l was 94%.

The analysis data of the product 2l was as follows $^1$H-NMR (400 MHz, CDCl$_3$) δ 7.21(dd, J=1.2 Hz, 5.2 Hz, 1H), 6.97(dd, J=3.6 Hz, 4.8 Hz, 1H), 6.92(dt, J=1.2 Hz, 3.6 Hz, 1H), 5.19(dd, J=3.2 Hz, 8.4 Hz, 1H), 4.06(br s, 2H), 3.03-2.96(m, 1H), 2.90-2.84(m, 1H), 2.74-2.59(m, 2H), 2.02-1.96(m, 1H), 1.92-1.83(m, 1H), 1.11(t, J=7.2 Hz, 3H);

$^{13}$C-NMR (100 MHz, CDCl$_3$) δ 149.9, 126.5, 123.6, 122.2, 71.9, 47.8, 43.8, 37.3, 15.1;

IR (KBr, v/cm$^{-1}$): 3265, 2943, 2898, 1481, 1378, 1110, 1064, 949, 909, 875, 834, 816, 703;

HRMS (ESI-MS): C$_9$H$_{16}$NOS [M+H]$^+$ theoretically calculated: 186.0953, obtained: 186.0949

The amine group in the product 2l was acetylated to give the following compound 3l. The ee value of 3l was 98% as determined by chiral HPLC. Accordingly, the product 2l had an ee value of 98%.

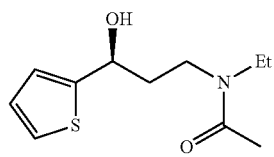

3l

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=90:10. The flow rate of the mobile phase was 1.0 mL/min, t$_{major}$=15.7 min, t$_{minor}$=19.1 min.

The analysis data of the compound 3l was as follows.

$^1$H-NMR (400 MHz, CDCl$_3$) δ 7.23(dd, J=1.6 Hz, 4.8 Hz, 0.2H), 7.19-7.18(m, 0.8H), 6.96-6.92(m, 2H) 4.99(br s, 1H), 4.93(t, J=6.4 Hz, 0.2H), 4.79(d, J=3.2 Hz, 10.0 Hz, 0.8H), 400-3.93(m, 0.8H), 3.40-3.32(m, 1.7H), 3.28-3.19(m, 0.8H), 3.17-3.11(m, 0.8H), 2.09(s, 2.2H), 2.07-2.01(m, 1.8H), 1.96-1.88(m, 1H), 1.20 (t, J=7.2 Hz, 2.4H), 1.08(t, J=7.2 Hz, 0.6H);

$^{13}$C-NMR (100 MHz, CDCl$_3$) δ 172.1, 148.3, 127.0, 126.7, 124.9, 124.3, 124.0, 123.1, 67.5, 66.6, 45.1, 43.8, 41.9, 40.6, 38.5, 37.7, 21.7, 21.3, 14.1, 13.2;

IR (KBr, v/cm$^{-1}$): 3334, 2988, 2918, 2849, 1737, 1620, 1488, 1424, 1373, 1285, 1229, 1070, 1035, 703;

HRMS (ESI-MS): C$_{11}$H$_{18}$NO$_2$S [M+H]$^+$ theoretically calculated: 228.1058, obtained: 228.1059

Example 13

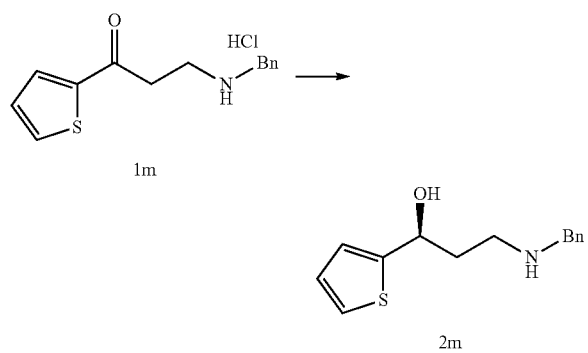

Into a 50 mL reaction vial, 1.5 mg of [Rh((S,S)-QuinoxP*)(cod)]SbF$_6$ as a catalyst, 281.1 mg of N-benzyl-3-carbonyl-3-(2-thienyl)propylamine hydrochloric (substrate 1m), 112.2 mg of potassium tert-butoxide, and 246.4 mg of cerium chloride [ketone:catalyst:alkali:additive=500:1:500:500 (molar ratio)] were added separately. The reaction vial was placed into a hydrogenation autoclave, and was ventilated with hydrogen gas by vacuum-pumping for 3 times. 5 mL of degassed tetrahydrofuran was added under protection of hydrogen gas. Finally the hydrogen pressure was adjusted to 20 bar and the reaction mixture was vigorously stirred for 12 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2m as pale yellow solid. The yield of the product 2m was 92%.

The analysis data of the product 2m was as follows.

$^1$H-NMR (400 MHz, CDCl$_3$) δ 7.38-7.28(m, 5H), 7.23 (dd, J=1.2 Hz, 5.2 Hz, 1H), 6.99(dd, J=3.2 Hz, 5.2 Hz, 1H), 6.94(dt, J=1.2 Hz, 3.6 Hz, 1H), 5.24(dd, J=3.2 Hz, 8.4 Hz, 1H), 3.83(q, J=12.8 Hz, 10.4 Hz, 2H), 309-3.04(m, 1H), 2.96-2.90(m, 1H), 2.09-2.02(m, 1H), 1.99-1.90(m, 1H);

$^{13}$C-NMR (100 MHz, CDCl$_3$) δ 149.6, 139.1, 128.6, 128.3, 127.3, 126.6, 123.8, 122.4, 72.0, 53.8, 47.6, 37.4;

IR (KBr, v/cm$^{-1}$); 3266, 2902, 2851, 2706, 1490, 1453, 1437, 1100, 1075, 1024, 896, 792, 746, 716, 693;

HRMS (ESI-MS); C$_{14}$H$_{18}$NOS [M+H]$^+$ theoretically calculated: 248.1109, obtained: 248.1106

The amine group in the product 2m was acetylated to give the following compound 3m. The ee value of 3m was 98% as determined by chiral HPLC. Accordingly, the product 2m had an ee value of 98%;

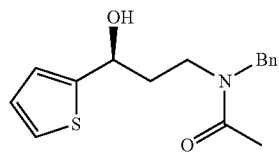

The HPLC analysis was carried out under the condition as follows. A chiral chromatography column of Daicel chiralpak AD-H manufactured by Daicel Corp. (Japan) was used. The mobile phase was n-hexane:iso-propanol (volumetric ratio)=90:10. The flow rate of the mobile phase was 1.0 mL/min, t$_{major}$=23.8 min, t$_{minor}$=27.2 min.

The analysis data of the compound 3m was as follows.

$^1$H-NMR (400 MHz, CDCl$_3$) δ 7.42-7.19(m, 6H), 6.98-6.92(m, 1H), 4.91-4.86(m, 1H), 4.66-4.47(m, 2H), 4.09-4.02 (m, 0.8H), 3.41-3.37(m, 0.4H), 3.24-3.18(m, 0.8H), 2.18(s, 0.7H), 2.16(s, 2.3H), 2.09-2.00(m, 1H), 1.97-1.89(m, 1H);

$^{13}$C-NMR (100 MHz, CDCl$_3$) δ 173.1, 171.3, 148.3, 137.9, 136.3, 129.3, 128.8, 128.4, 128.1, 127.6, 127.0, 126.8, 126.5, 125.1, 124.3, 124.1, 123.2, 67.5, 66.8, 52.5, 48.4, 44.7, 42.8, 37.9, 37.3, 21.8, 21.6;

IR (KBr, v/cm$^{-1}$): 3362, 3029, 2921, 2850, 1737, 1624, 1422, 1366, 1288, 1232, 1169, 1076, 1028, 982, 729, 698;

HRMS (ESI-MS): C$_{16}$H$_{20}$NO$_2$S [M+H]$^+$ theoretically calculated: 290.1295, obtained: 290.1296

Example 14

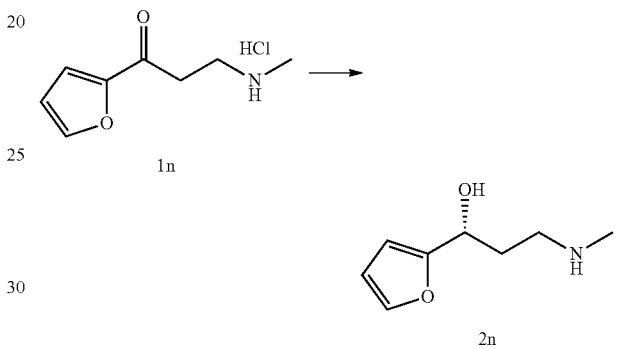

Into a 50 mL reaction vial 1.5 mg of [Rh((R,R)-QuinoxP*)(cod)]SbF$_6$ as a catalyst, 1891 mg of N-methyl-3-carbonyl-3-(2-furyl)propylamine hydrochloride (substrate 1n), 1122 mg of potassium tert-butoxide. and 2464 mg of cerium chloride [ketone:catalyst:alkali:additive=5000:1:5000:5000 (molar ratio)] were added separately. The reaction vial was placed into a hydrogenation autoclave, and was ventilated with hydrogen gas by vacuum-pumping for 3 times. 5 mL of degassed tetrahydrofuran was added under protection of hydrogen gas. Finally the hydrogen pressure was adjusted to 20 bar and the reaction mixture was vigorously stirred for 12 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2n as dark yellow oil. The yield of the product 2n was 95%.

The analysis data of the product 2n was as follows.

$^1$H-NMR (400 MHz, CDCl$_3$) δ 7.35(s, 1H), 6.32(dd, J=1.6 Hz, 7.2 Hz, 1H), 6.24(d, J=7.2 Hz, 1H), 4.93(t, J=6.0 Hz, 1H), 2.94-2.80(m, 2H), 2.88(br s, 2H), 2.43(s, 3H), 1.97-1.92(m, 2H).

$^{13}$C-NMR (100 MHz, CDCl$_3$) δ 141.7, 110.2, 105.5, 69.7, 50.3, 36.2, 33.3;

IR (KBr, v/cm$^{-1}$): 3300, 2942, 2853, 1619, 1540, 1488, 1387, 1306, 1273, 1228, 1150, 1066, 1010, 884, 813, 739, 600;

HRMS (ESI-MS): C$_8$H$_{14}$NO$_2$ [M+H]$^+$ theoretically calculated: 156.1025, obtained: 156.1025

The amine group in the product 2n was acetylated to give the following compound 3n. The ee value of 3n was 99% as determined by chiral HPLC. Accordingly, the product 2n had an ee value of 99%.

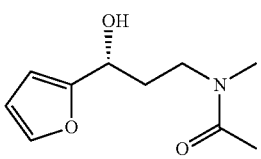

3n

The HPLC analysis was carried out under the condition as follows. A chiral chromatography column of Daicel chiralpak AD-H manufactured by Daicel Corp. (Japan) was used. The mobile phase was n-hexane:iso-propanol (volumetric ratio)=95:5. The flow rate of the mobile phase was 1.0 mL/min, $t_{minor}$=44.4 min, $t_{major}$=48.6 min.

The analysis data of the compound 3n was as follows.

$^1$H-NMR (400 MHz, CDCl$_3$) δ 7.32-7.29(m, 1H), 6.28-6.26(m, 1H), 6.19(d, J=3.2 Hz, 1H), 4.72(br s, 1H), 4.62 (t, J=6.8 Hz, 0.3H), 4.55(t, J=6.8 Hz, 0.7H), 3.87-3.80(m, 0.8H), 3.45-3.32(m, 0.4H), 3.22-3.16(m, 0.8H), 2.93(s, 2.2H), 2.85(s, 0.8H), 2.02(s, 1H), 2.00(s, 2H), 2.00-1.95(m, 2H);

$^{13}$C-NMR (100 MHz, CDCl$_3$) δ 172.4, 171.2, 156.6, 142.1, 141.8, 110.4, 110.4, 106.1, 105.7, 64.7, 64.4, 47.4, 44.3, 36.5, 34.0, 33.3, 32.8, 21.7, 21.3;

IR (KBr, v/cm$^{-1}$); 3362, 2931, 1621, 1497, 1404, 1150, 1065, 1010, 742, 599;

HRMS (ESI-MS); C$_{10}$H$_{15}$NO$_3$Na [M+Na]$^+$ theoretically calculated: 220.0950, obtained: 220.0951

Example 15

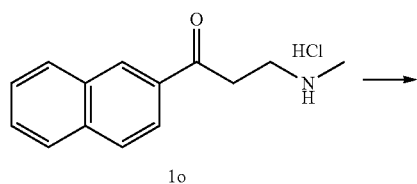

1o

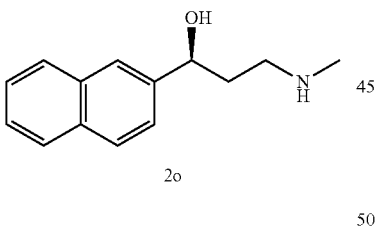

2o

Into a 50 mL reaction vial, 1.5 mg of [Rh((S,S)-QuinoxP*)(cod)]SbF$_6$ as a catalyst, 2491 mg of N-methyl-3-carbonyl-3-(2-naphthyl)propylamine hydrochloride (substrate 1o), 1122 mg of potassium tert-butoxide, and 2464 mg of cerium chloride [ketone:catalyst:alkali:additive=5000:1:5000:5000 (molar ratio)] were added separately. The reaction vial was placed into a hydrogenation autoclave, and was ventilated with hydrogen gas by vacuum-pumping for 3 times. 15 mL of degassed tetrahydrofuran was added under protection of hydrogen gas. Finally the hydrogen pressure was adjusted to 20 bar and the reaction mixture was vigorously stirred for 6 hour at the temperature of 25° C. After the reaction was terminated, the mixture was concentrated by distillation to remove the solvent. The residue was subjected to column chromatography using alkaline alumina (methylene chloride V1/methanol V2=20/1) to give a product 2o as white solid. The yield of the product 2o was 93%.

The analysis data of the product 2o was as follows.

$^1$H-NMR (400 MHz, CDCl$_3$) δ 7.86-7.80(m, 4H), 7.48-7.42(m, 3H), 5.10(dd, J=3.2 Hz, 8.4 Hz, 1H), 3.52(br s, 2H), 2.92-2.84(m, 2H), 2.45(s, 3H), 2.00-1.93(m, 1H), 1.87-1.80 (m, 1H);

$^{13}$C-NMR (100 MHz, CDCl$_3$) δ 142.8, 133.6, 133.0, 128.2, 128.1, 127.8, 126.1, 125.7, 124.4, 124.3, 75.8, 50.6, 36.9, 36.2.

The amine group in the product 2o was acetylated to give the following compound 3o. The ee value of 3o was 98% as determined by chiral HPLC. Accordingly, the product 2o had an ee value of 98%.

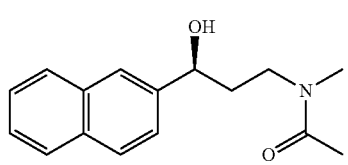

3o

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=95:5. The flow rate of the mobile phase was 1.0 mL/min, $t_{major}$=35.1 min, $t_{minor}$=46.9 min.

The analysis data of the compound 3o was as follows.

$^1$H-NMR (400 MHz, CDCl$_3$) δ 7.79-7.72(m, 4H), 7.45-7.39(m, 3H), 4.85(br s, 1H), 4.74(t, J=6.4 Hz, 0.2H), 4.68 (dd, J=3.6 Hz, 10.4 Hz, 0.8H), 3.99-3.92(m, 0.8H), 3.45-3.27(m, 0.4H), 3.15-3.09(m, 0.8H), 2.90(s, 2.1H), 2.83(s, 0.9H), 2.00(s, 2.1H), 1.99(s, 0.9H), 1.97-1.92(m, 1H), 1.89-1.82(m, 1H);

$^{13}$C-NMR (100 MHz, CDCl$_3$) δ 172.3, 171.2, 142.0, 141.8, 133.5, 133.5, 133.2, 132.9, 128.6, 128.2, 128.1, 127.9, 127.8, 126.5, 126.2, 126.1, 125.8, 124.6, 124.4, 124.3, 124.0, 71.3, 70.4, 47.7, 44.9, 37.4, 36.8, 36.5, 33.3, 21.8, 21.3.

Example 16

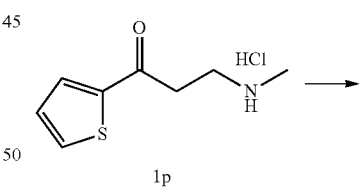

1p

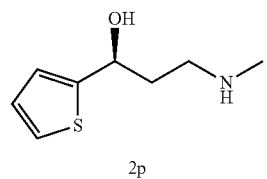

2p

Into a 50 mL reaction vial, 1.5 mg of [Rh((S,S)-QuinoxP*)(cod)]SbF$_6$ as a catalyst, 410.9 mg of N-methyl-3-carbonyl-3-(2-thienyl)propylamine hydrochloride (substrate 1p), 224.4 mg of potassium tert-butoxide, and 638.2 mg of zinc iodide [ketone:catalyst:alkali:additive=1000:1:1000:1000 (molar ratio)] were added separately. The reaction vial was placed into a hydrogenation autoclave, and was ventilated with hydrogen gas by vacuum-pumping for 3 times. 10 mL of degassed tetrahydrofuran was added under protection of hydrogen gas. Finally the hydrogen pressure was adjusted to 20 bar. The reaction mixture was vigorously stirred for 12 hour at the temperature of 25° C. After the reaction was terminated, the mixture was concentrated by distillation to remove the solvent. The residue was subjected to column chromatography using alkaline alumina (methylene chloride V1/methanol V2=20/l) to give a product 2p as yellow oil. The yield of the product 2p was 83%.

The analysis data of the product 2p was as follows.

$^1$H-NMR (400 MHz, CDCl$_3$) δ 7.18(dd, J=1.2 Hz, 4.8 Hz, 1H), 6.94(t, J=6.0 Hz, 1H), 6.90(d, J=3.6 Hz, 1H), 5.15(dd, J=3.2 Hz, 8.4 Hz, 1H), 3.93(br s, 2H), 2.94-2.88(m, 1H), 2.85-2.79(m, 1H), 2.40(s, 3H), 1.99-1.84(m, 2H);

13C-NMR (100 MHz, CDCl3) δ 149.9, 126.8, 123.9, 122.6, 71.8, 50.2, 37.2, 36.1.

The amine group in the product 2p was acetylated to give the following compound 3p. The ee value of 3p was 94% as determined by chiral HPLC. Accordingly, the product 2p had an ee value of 94%.

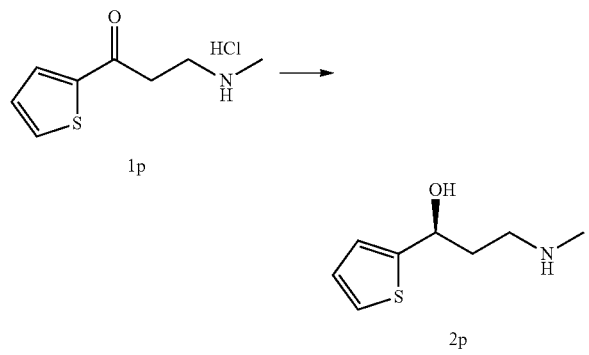

3p

The HPLC analysis was carried out under the condition as follows. A chiral chromatography column of Daicel chiralpak OD-H manufactured by Daicel Corp. (Japan) was used. The mobile phase was n-hexane:iso-propanol (volumetric ratio)=97:3. The flow rate of the mobile phase was 1.2 mL/min, $t_{major}$=77.2 min, $t_{minor}$=91.1 min.

The analysis data of the compound 3p was as follows.

$^1$H-NMR (400 MHz, CDCl$_3$) δ 7.23(dd, J=1.6 Hz, 4.4 Hz, 0.2H), 7.19-9.18(m, 0.8H), 6.95-6.91(m, 2H), 4.90(t, J=6.4 Hz, 0.2H), 4.84(br s, 1H), 4.78(dd, J=3.6 Hz, 9.6 Hz, 0.8H), 4.03-3.96(m, 0.8H), 3.49-3.34(m, 0.4H), 3.16-3.10(m, 0.8H), 2.99(s, 2.3H), 2.88(s, 0.7H), 2.09-2.01(m, 1H), 2.05 (s, 3H), 1.96-1.89(m, 1H);

$^{13}$C-NMR (100 MHz, CDCl$_3$) δ 172.5, 148.2, 127.0, 126.7, 124.9, 124.3, 124.0, 123.2, 67.2, 66.5, 47.5, 44.6, 37.7, 36.7, 33.4, 21.8, 21.3.

Example 17

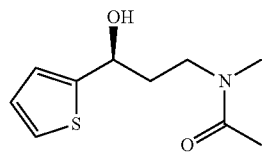

1p

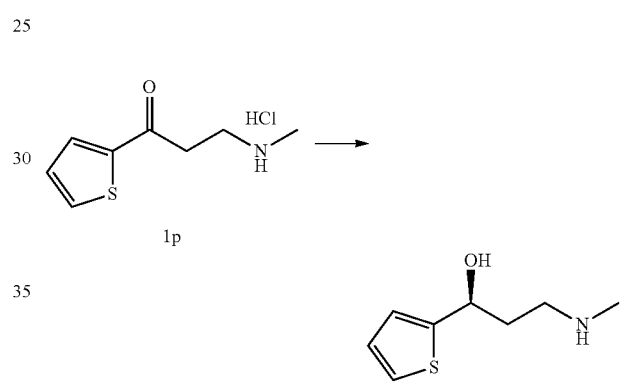

Into a 50 mL reaction vial, 1.5 mg of [Rh((S,S)-QuinoxP*)(cod)]SbF$_6$ as a catalyst, 4109 mg of N-methyl-3-carbonyl-3-(2-thienyl)propylamine hydrochloride (substrate 1p), 2244 mg of potassium tert-butoxide, and 4929 mg of cerium chloride [ketone:catalyst:alkali:additive=10000:1:10000:10000 (molar ratio)] were added separately. The reaction vial was placed into a hydrogenation autoclave, and was ventilated with hydrogen gas by vacuum-pumphig for 3 times. 20 mL of degassed tetrahydrofuran was added under protection of hydrogen gas. Finally the hydrogen pressure was adjusted to 20 bar and the reaction mixture was vigorously stirred for 12 hour at the temperature of 25° C. After the reaction was terminated, the mixture was concentrated by distillation to remove the solvent. The residue was subjected to column chromatography using alkaline alumina (methylene chloride V1/methanol V2=20/l) to give a product 2p as yellow oil. The yield of the product 2p was 97%. The amine group in the product 2p was acetylated to give the above compound 3p. The ee value of 3p was 99% as determined with HPLC by the same method as that recorded in example 16. Accordingly, the product 2p as the product obtained in example 17 had an ee value of 99%.

Example 18

1.5 mg of [Rh((S,S)-QuinoxP*)(cod)]SbF$_6$ as a catalyst, 16.44 mg of N-methyl-3-carbonyl-3-(2-thienyl)propylamine hydrochloride (substrate 1p), 9.98 mg of potassium tert-butoxide, and 9.86 mg of cerium chloride [ketone:catalyst:alkali:additive=20000:1:20000:20000 (molar ratio)] were placed into the F4 lining of a hydrogenation autoclave, which was then ventilated with hydrogen gas by vacuum-pumphig for 3 times. 200 mL of degassed tetrahydrofuran was added under protection of hydrogen gas. Finally the hydrogen pressure was adjusted to 50 bar and the reaction mixture was vigorously stirred for 48 hour at the temperature of 25° C. After the reaction was terminated, the mixture was concentrated by distillation to remove the solvent. The residue was subjected to column chromatography using alkaline alumina (methylene chloride V1/methanol V2=20/l) to give a product 2p as an oil. The yield of the product 2p was 76%. The amine group in the product 2p was acetylated to give the above compound 3p. The ee value of 3p was 97% as determined with HPLC by the same method as that recorded in example 16. Accordingly, the product 2p as the product obtained in example 18 had an ee value of 97%.

Comparative Example 1

Into a 50 mL reaction vial, 1.5 mg of [Rh((S,S)-BenzP*)(cod)]SbF$_6$ as a catalyst, 80.3 mg of N-methyl-3-carbonyl- 3-phenyl propylamine hydrochloride (substrate 1a) and 27.7 mg of potassium carbonate [ketone:catalyst:alkali=200:1:100 (molar ratio)] were added separately. The reaction vial was placed into a hydrogenation autoclave, and was ventilated with hydrogen gas by vacuum-pumping for 3 times. 2 mL of degassed ethyl acetate was added under protection of hydrogen gas. Finally the hydrogen pressure was adjusted to 50 bar and the reaction mixture was vigorously stirred for 1 hour at the temperature of 50° C. After the reaction was terminated, the mixture was concentrated by distillation to remove the solvent. The residue was subjected to column chromatography using alkaline alumina (methylene chloride V1/methanol V2=20/1) to give a product 2a as a pale yellow oil. The yield of the product 2a was 36%.

The amine group in the product 2a was acetylated to give the above compound 3a. The ee value of 3a was 64% as determined with chiral HPLC by the same method as that recorded in Example 1. Accordingly, the product 2a as the product obtained in Comparative Example 1 had an ee value of 63%.

Application Example 1

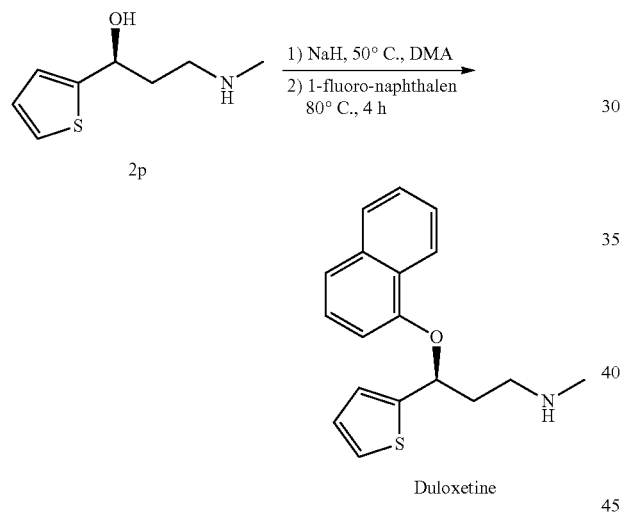

8.56 g of (S)-N-methyl-3-hydroxy-3-(2-thienyl)propylamine 2p was dissolved in 50 mL of N,N-dimethyl acetamide. 2.40 g of sodium hydride was added slowly in an ice bath. Following the addition the reaction mixture was heated at the temperature of 50° C. to allow reaction for 2 hours. Subsequently, 14.60 g of 1-fluoro naphthalene was added. The reaction was allowed for 4 hours at the temperature of 80° C. After the reaction was completed the resultant was allowed to cool down. Toluene was added for dilution and the resultant mixture was exacted with toluene and water. The organic phases were combined, concentrated, and dried to give an oily liquid. The resultant oily liquid was subjected to column chromatography to give 9.65 g of oily liquid. The yield of Duloxetine as the product was 65%.

The analysis data of Duloxetine as the product was as follows.

[α]$_D^{25}$=−110.7 (c 0.9, CHCl$_3$);

$^1$H-NMR (400 MHz, CDCl$_3$): 8.35-8.33 (m, 1H), 7.81-7.78 (m, 1H), 7.52-7.48 (m, 2H), 7.42 (d, J=8.4 Hz, 1H), 7.29-7.27 (m, 1H), 7.25-7.21 (m, 1H), 7.20-7.09 (m, 1H) 6.92 (dd, J=3.6 Hz, 5.2 Hz, 1H), 6.90 (d, J=7.6 Hz, 1H), 5.86 (dd, J=5.2 Hz, 7.6 Hz, 1H), 3.28-3.22 (m, 2H), 2.65-2.62 (m, 1H), 2.55 (s, 3H), 2.48-2.43 (m, 1H).

$^{13}$C-NMR (100 MHz CDCl$_3$): 153.2, 145.0, 134.4, 127.3, 126.4, 126.2, 125.9, 125.5, 125.0, 124.6, 121.9, 120.4, 106.7, 74.6, 48.1, 38.7, 36.5.

Specific examples of the present invention have been described above. It is to be understood that the present invention is not limited to the above specific examples and A person skilled in this art can make various changes or modifications, which are all within the scope of the claims, without affecting the inventive substance of the present invention.

The invention claimed is:

1. A method for preparing a chiral γ-secondary amino alcohol, comprising the steps of:

adding into a solvent an acid addition salt of β-secondary amino ketone represented by the general formula (1), an alkali, a metal salt additive and a diphosphine-rhodium complex to react in hydrogen atmosphere, so as to obtain a chiral compound of γ-secondary amino alcohol represented by the general formula (2),

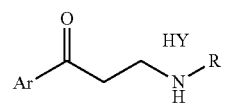 (1)

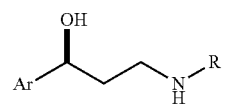 (2)

in the general formulas (1) and (2), Ar represents an aryl group with or without substituent group(s), R represents an alkyl group or an aralkyl group, and HY represents an acid; and wherein:

the diphosphine-rhodium complex is [Rh(L)(L')]X, wherein

L is any one chiral diphosphine ligand selected from the group consisting of (R,R)-QuinoxP*, (R,R)-BenzP*, (R,R)-Miniphos, (S,S)-Bi sP*, (S,S)-QuinoxP*, (S,S)-BenzP*, (S,S)-Miniphos and (R,R)-BisP* shown as follows,

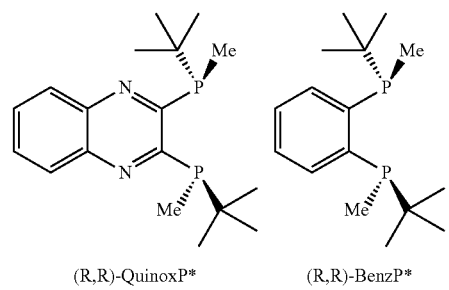

(R,R)-QuinoxP*      (R,R)-BenzP*

-continued

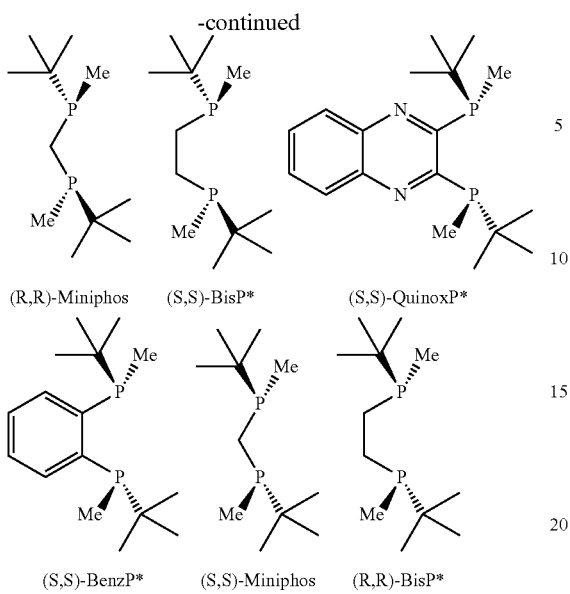

(R,R)-Miniphos  (S,S)-BisP*  (S,S)-QuinoxP*

(S,S)-BenzP*  (S,S)-Miniphos  (R,R)-BisP*

L' is any one auxiliary diene ligand selected from the group consisting of 1,5-cyclooctadiene and 2,5-norbornadiene, X is any one anion selected from the group consisting of $SbF_6^-$ and $BF_4^-$.

2. The method for preparing a chiral γ-secondary amino alcohol according to claim 1, wherein:
in the general formulas (1) and (2),
Ar is any one selected from the group consisting of phenyl, 2-methylphenyl, 3-methylphenyl, 4-methylphenyl, 2-methoxyphenyl, 3-methoxyphenyl, 4-methoxyphenyl, 2-ethoxyphenyl, 3-ethoxyphenyl, 4-ethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 1-naphthyl, 2-naphthyl, 2-trifluoromethylphenyl, 3-trifluoromethylphenyl, 4-trifluoromethylphenyl, 2-furyl, 2-thienyl, 3,4-dimethoxyphenyl, 3,4-dimethylphenyl, 3,4-dichlorophenyl and 3,4-methylenedioxyphenyl;
R is any one selected from the group consisting of methyl, ethyl, propyl, iso-propyl, butyl, iso-butyl, tert-butyl, pentyl, iso-pentyl, neo-pentyl, hexyl, heptyl, octyl and benzyl.

3. The method for preparing a chiral γ-secondary amino alcohol according to claim 1, wherein:
in the general formula (1), HY is any one selected from the group consisting of hydrochloric acid, sulfuric acid, phosphoric acid, tartaric acid, p-methylbenzenesulfonic acid, trifluoromethanesulfonic acid, salicylic acid, tetrafluoroboric acid, hexafluorophosphoric acid and hexafluoroantimonic acid.

4. The method for preparing a chiral γ-secondary amino alcohol according to claim 1, wherein:
the molar ratio of the diphosphine-rhodium complex to the acid addition salt of β-secondary amino ketone represented by the general formula (1) is 1/200~1/20000.

5. A method for preparing a chiral γ-secondary amino alcohol, comprising the steps of:
adding into a solvent an acid addition salt of β-secondary amino ketone represented by the general formula (1), an alkali, a metal salt additive and a diphosphine-rhodium complex to react in hydrogen atmosphere, so as to obtain a chiral compound of γ-secondary amino alcohol represented by the general formula (2),

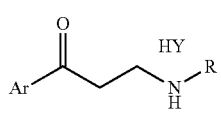

(1)

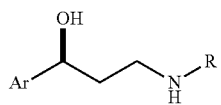

(2)

in the general formulas (1) and (2), Ar represents an aryl group with or without substituent group(s), R represents an alkyl group or an aralkyl group, and HY represents an acid; and
the metal salt additive is any one selected from the group consisting of zinc acetate, cerium chloride, zinc trifluoromethane sulfonate, copper chloride, copper acetate, zinc iodide, copper iodide, zinc chloride, magnesium sulfate, ferric chloride and aluminum chloride.

6. The method for preparing a chiral γ-secondary amino alcohol according to claim 1, wherein:
the alkali is any one selected from the group consisting of potassium hydroxide, sodium hydroxide, potassium carbonate, sodium carbonate, cesium carbonate, potassium bicarbonate, sodium bicarbonate, potassium phosphate, dipotassium phosphate, monopotassium phosphate, triethylamine, sodium acetate and potassium tert-butoxide.

7. The method for preparing a chiral γ-secondary amino alcohol according to claim 1, wherein:
the solvent is a polar solvent.

8. The method for preparing a chiral γ-secondary amino alcohol according to claim 7, wherein:
the solvent is any one or two or more selected from the group consisting of ethyl acetate, methylene chloride, tetrahydrofuran, methanol, ethanol, isopropanol and trifluoroethanol.

9. The method for preparing a chiral γ-secondary amino alcohol according to claim 1, wherein:
the pressure of hydrogen is 10~100 bar in the hydrogen atmosphere, the reaction temperature is −20~100° C., and the reaction time is 1~48 hours.

10. The method for preparing a chiral γ-secondary amino alcohol according to claim 2, wherein:
the molar ratio of the diphosphine-rhodium complex to the acid addition salt of β-secondary amino ketone represented by the general formula (1) is 1/200~1/20000.

11. The method for preparing a chiral γ-secondary amino alcohol according to claim 2, wherein:
the metal salt additive is any one selected from the group consisting of zinc acetate, cerium chloride, zinc trifluoromethane sulfonate, copper chloride, copper acetate, zinc iodide, copper iodide, zinc chloride, magnesium sulfate, ferric chloride and aluminum chloride.

12. The method for preparing a chiral γ-secondary amino alcohol according to claim 2, wherein:
the alkali is any one selected from the group consisting of potassium hydroxide, sodium hydroxide, potassium carbonate, sodium carbonate, cesium carbonate, potassium bicarbonate, sodium bicarbonate, potassium phosphate, dipotassium phosphate, monopotassium phosphate, triethylamine, sodium acetate and potassium tert-butoxide.

13. The method for preparing a chiral γ-secondary amino alcohol according to claim 2, wherein:
the solvent is a polar solvent.

14. The method for preparing a chiral γ-secondary amino alcohol according to claim 2, wherein:
the pressure of hydrogen is 10~100 bar in the hydrogen atmosphere, the reaction temperature is −20~100° C., and the reaction time is 1~48 hours.

\* \* \* \* \*